(12) United States Patent
Gibson et al.

(10) Patent No.: US 11,911,563 B2
(45) Date of Patent: Feb. 27, 2024

(54) MOISTURE PERMEABLE CONDUIT FOR A BREATHING CIRCUIT

(71) Applicant: Plastiflex Group, Paal-Beringen (BE)

(72) Inventors: Diane Gibson, Clydebank (GB); Jeno Kurja, Paal-Beringen (BE)

(73) Assignee: Plastiflex Group, Paal-Beringen (BE)

( * ) Notice: Subject to any disclaimer, the term of this patent is extended or adjusted under 35 U.S.C. 154(b) by 0 days.

(21) Appl. No.: 17/287,582

(22) PCT Filed: Nov. 6, 2019

(86) PCT No.: PCT/EP2019/080441
§ 371 (c)(1),
(2) Date: Apr. 22, 2021

(87) PCT Pub. No.: WO2020/094741
PCT Pub. Date: May 14, 2020

(65) Prior Publication Data
US 2021/0316102 A1    Oct. 14, 2021

(30) Foreign Application Priority Data
Nov. 8, 2018    (EP) ..................................... 18205267

(51) Int. Cl.
*A61M 16/08* (2006.01)
*B29C 53/58* (2006.01)
(Continued)

(52) U.S. Cl.
CPC ........... *A61M 16/08* (2013.01); *B29C 53/581* (2013.01); *B29C 53/585* (2013.01);
(Continued)

(58) Field of Classification Search
CPC .. A61F 2005/002; A61F 5/003; A61F 5/0036; A61F 5/0043; A61F 5/0046;
(Continued)

(56) References Cited

U.S. PATENT DOCUMENTS 5,637,168 A    6/1997    Carlson
6,523,538 B1   2/2003    Wikefeldt
(Continued)

FOREIGN PATENT DOCUMENTS

EP    1396276    3/2004
EP    1396277    3/2004
(Continued)

OTHER PUBLICATIONS

DuPont Hytrel 5556, Thermoplastic Polyester Elastomer. Product information. 2017.

*Primary Examiner* — Annette Dixon
(74) *Attorney, Agent, or Firm* — N.V. Nederlandsch Octrooibureau

(57) ABSTRACT

There is provided a flexible, helically wound conduit for a breathing circuit. The conduit includes an inlet, an outlet, and an enclosing wall defining a flow passage between the inlet and the outlet, wherein at least a region of the enclosing wall is permeable to water vapor and one or more of $O_2$ and $CO_2$. The axial tensile strength of the enclosing wall is greater than 40N. Further provided are limbs comprising the conduit, a method of manufacturing the conduit and the use of the conduit to remove water vapor and/or $CO_2$ from gas exhaled by a patient.

19 Claims, 12 Drawing Sheets

(51) Int. Cl.
*B29C 53/78* (2006.01)
*B29C 53/80* (2006.01)
*B29C 53/84* (2006.01)

(52) U.S. Cl.
CPC ........ *B29C 53/785* (2013.01); *B29C 53/8083* (2013.01); *B29C 53/845* (2013.01)

(58) Field of Classification Search
CPC ............ A61M 13/003; A61M 16/0078; A61M 16/0081; A61M 16/01; A61M 16/06; A61M 16/08; A61M 16/0808; A61M 16/0816; A61M 16/0833; A61M 16/085; A61M 16/0858; A61M 16/0875; A61M 16/0883; A61M 16/10; A61M 16/105; A61M 16/1095; A61M 16/161; A61M 16/22; A61M 2016/0027; A61M 2016/003; A61M 2016/0033; A61M 2205/0216; A61M 2205/3368; A61M 2205/59; A61M 2205/6081; A61M 2206/11; A61M 2207/00; A61M 2209/06; B29C 2053/365; B29C 48/06; B29C 48/08; B29C 48/131; B29C 48/151; B29C 48/266; B29C 53/36; B29C 53/581; B29C 53/582; B29C 53/60; B29C 53/607; B29C 63/0013; B29C 65/00; B29C 65/40; B29C 65/48; B29C 66/1122; B29C 66/43; B29C 66/4322; B29C 66/4329; B29C 66/49; B29C 66/496; B29C 66/71; B29K 2021/00; B29K 2023/065; B29K 2067/003; B29K 2105/06; B29K 2267/003; B29L 2031/753; C08L 2205/08; C08L 2205/16; C08L 2205/22; C08L 23/10; C08L 23/16; C08L 2312/00; C08L 27/06; C08L 51/06; C08L 61/28; C08L 67/00; C08L 77/10; F16L 11/115; F16L 9/16; Y10S 128/911; Y10S 138/08; Y10T 29/49826

See application file for complete search history.

(56) References Cited

U.S. PATENT DOCUMENTS

| | | | |
|---|---|---|---|
| 8,037,882 | B2 | 10/2011 | Smith et al. |
| 10,159,814 | B2 | 12/2018 | Smith et al. |
| 10,252,017 | B2 | 4/2019 | Smith et al. |
| 10,399,038 | B2 * | 9/2019 | Oborný ................ B01D 63/061 |
| 2004/0099268 | A1 | 5/2004 | Smith |
| 2004/0194781 | A1 * | 10/2004 | Fukunaga ............. A61M 16/01 |
| | | | 128/911 |
| 2016/0100970 | A1 * | 4/2016 | Brister .................. A61F 5/0046 |
| | | | 606/192 |
| 2017/0080175 | A1 * | 3/2017 | Gray ..................... B29C 53/581 |
| 2018/0280650 | A1 | 10/2018 | Hlopick |
| 2021/0077765 | A1 * | 3/2021 | Peiris ................ A61M 16/1095 |

FOREIGN PATENT DOCUMENTS

| | | | |
|---|---|---|---|
| EP | 1477200 | | 11/2004 |
| EP | 1658330 B1 * | 11/2007 | .......... B29C 48/131 |
| WO | 2016048172 A1 | | 3/2016 |
| WO | 2017213523 | | 12/2017 |

* cited by examiner

MOISTURE PERMEABLE CONDUIT FOR A BREATHING CIRCUIT

FIELD OF THE INVENTION

This invention relates to a conduit for a breathing circuit comprising an inlet, an outlet, and an enclosing wall defining a flow passage between said inlet and said outlet wherein said enclosing wall is permeable to water vapor and one or more further breathing gases, in particular $CO_2$. This invention also relates to limbs comprising the conduit, a method of manufacturing the conduit and the use of the conduit to remove water vapor and/or $CO_2$ from gas inhaled or exhaled by a patient.

BACKGROUND OF THE INVENTION

A hose or conduit for carrying inspiratory or expiratory gas to or from a person, usually a patient, may be used for a variety of purposes such as anesthesia, life support, medication delivery, prevention of sleep apnea etc. In these applications and others, managing the humidity and temperature of the gases flow is crucial.

As an example for a conduit comprised in the inspiratory limb of a breathing apparatus, but not limited thereto, serves the case of a patient who is diagnosed with Obstructive Sleep Apnea (OSA). In OSA patients, the tongue and uvula partly or completely block air from moving down the throat to the lungs. During Continuous Positive Airway Pressure (CPAP) treatment an air flow is delivered to the patient, allowing air to pass down the throat of the patient to the lungs. Due to the high air flow rates, the airways are not able to deliver sufficient heat and moisture. The result is that the airways lose moisture and finally will show symptoms like drying of the upper airways, dry nose, dry throat, headache, painful chest, damage of weak tissue around nose entry, bleeding nose, dry and damaged lips, infections of nose, throat and sinus.

As an example for a conduit comprised in the expiratory limb of a breathing apparatus, but not limited thereto, serves the case of a patient on a life support unit. The expired gas has high levels of relative humidity, often being (over) saturated, resulting in the formation of water droplets on the wall of the expiratory conduit. Condensation of water vapor in the expiratory conduit is highly undesirable as these may reach and distort measurements by sensing means comprised in the breathing apparatus, such as a $CO_2$ sensor monitoring if the patient is still alive.

In order to improve humidity management of inspired and/or expired gases, a number of measures have been developed in the prior art, such as the development of tubes, hoses or conduits which comprise a region of the enclosing wall which is permeable to water vapor but not permeable for liquid water or for respiratory gases. U.S. Pat. No. 7,140,366 describes such a limb for a breathing circuit, comprising an enclosing wall wherein at least a region of said enclosing wall is made of a material that allows the passage of water vapor without allowing the passage of liquid water or respiratory gases. U.S. Pat. No. 8,037,882 describes a conduit for a breathing circuit including a heater located within said conduit and at least a region of the conduit wall being of a "breathable material". A breathable material as used in U.S. Pat. No. 8,037,882 is a material that allows the passage of water vapor without allowing the passage of liquid water or respiratory gases.

The conduits known in the prior art and comprising a region of the enclosing wall which is permeable to water vapor but not permeable for liquid water or further respiratory gases suffer from several disadvantages. Alternative materials compatible for use in medical devices may suffer from the disadvantage that, in addition to desirable transmission of water vapor, these materials may also be highly permeable for further breathing gases, in particular carbon dioxide. For example, excessive migration of carbon dioxide inside-outwardly through the wall of an expiratory limb may hamper proper monitoring of the level of carbon dioxide in the exhaled breath of a patient depending on reliable controlling said level. For example, the mechanical strength (e.g. pull strength) is generally low, resulting in easy deformation or failure (e.g. tearing) of the tube, which is unacceptable from a patient safety perspective. Some commercially available conduits thus comprise an additional reinforcement measure such as a reinforcing member, layer or jacket which is not interesting from an environmental, process economical or aesthetical perspective. EP1396276 describes a limb for a breathing circuit comprising a thin walled conduit and a reinforcing member lying freely within said very thin walled conduit. EP1477200 describes a limb for a breathing circuit comprising a longitudinal reinforcement including a plurality of longitudinally extending threads spaced around the perimeter of the enclosing wall.

Additionally, the prior art tubes do not allow the passage of liquid water, which may be undesirable in case condensation is formed (e.g. due to rapidly changing environmental conditions such as ambient temperature and humidity levels or due to operation of the tube in extreme conditions).

In closed-system breathing apparatuses, exhaled $CO_2$ is removed using a $CO_2$ removal device, often referred to as a $CO_2$ scrubber. The $CO_2$ scrubber comprises a material which effectively traps $CO_2$ through means such as chemical conversion, absorption, adsorption etc. such as soda lime. The ability to absorb $CO_2$ of commonly employed materials such as soda lime or molecular sieves decreases while the breathing apparatus is in use as they become increasingly saturated. This results in the need to frequently replace and/or regenerate the $CO_2$ scrubber. Furthermore, manufacturers are downsizing anesthesia machines to reduce space requirements, improve ergonomics and/or improve mobility. This downsizing often entails equipping machines with smaller $CO_2$ scrubbers which is disadvantageous as this results in reduced operating times before requiring replacement/regeneration of the $CO_2$ scrubber (sometimes even requiring intraoperative replacement/regeneration). Finally, in the chemical reaction of $CO_2$ with soda lime, water is generated, and released into the circulating gas stream.

SUMMARY OF THE INVENTION

It is thus a first object of the present invention to provide an improved conduit for a breathing circuit that does not show one or more of the above-mentioned disadvantages.

It is a second object of the present invention to provide a flexible conduit for a breathing circuit which allows reliable $CO_2$ monitoring in e.g. the exhaled breathing gases of a patient while allowing passage of at least some $CO_2$ through the enclosing wall.

It is a third object of the present invention to provide a flexible conduit for a breathing circuit which has an improved mechanical strength, e.g. an improved axial tensile strength.

It is a fourth object of the present invention to provide a flexible conduit which allows the removal of liquid water from the flow passage of the conduit.

It is a fifth object of the present invention to provide a flexible conduit which can be more efficiently produced, e.g. using less material and/or at higher production speeds compared to production methods now in use for known breathable conduits.

One or more of the objects recited herein may be reached by the flexible conduit and/or method of production in accordance with the present invention, as defined by the claims.

It was surprisingly found that a flexible conduit could be provided which allows the passage of breathing gases such as $CO_2$ and/or $O_2$ without significantly affecting its suitability to be used in a closed breathing circuit or even life support applications. As will be shown in the appending examples, the conduit in accordance with the invention, even though it is permeable for breathing gases such as $CO_2$, surprisingly still allows accurate $CO_2$ measurements to be made. When the conduit of the invention is comprised in the expiratory limb of a life support breathing circuit, the permeability surprisingly does not interfere with for example monitoring of vital patient signs to determine if the patient is still alive. Furthermore, the present inventors surprisingly found that even though the conduit is permeable to breathing gases such as $CO_2$ and/or $O_2$ the pressure loss is sufficiently small so that monitoring of leaks using conventional pressure sensing means often included in breathing circuits is still possible. Since $CO_2$ passes through the wall of the conduit, this has further advantages in a closed-system breathing apparatus, for example the time before a $CO_2$ scrubber becomes saturated or needs to be regenerated/replaced, may be increased, and/or since less $CO_2$ reacts with soda lime, less water is generated and the likelihood of condensation, for example in the inspiratory limb is reduced.

In a first aspect of the invention there is thus provided a flexible conduit for a breathing circuit comprising an inlet, an outlet, and an enclosing wall defining a flow passage between said inlet and said outlet wherein the enclosing wall is permeable to water vapor and one or more further breathing gases.

Preferably, the flexible conduit of the invention comprises an enclosing wall, at least a region of which provides said permeability to water vapor and one or more further breathing gases. The further breathing gases may be oxygen or carbon dioxide. For example, said region may be at least permeable to water vapor and carbon dioxide.

Furthermore, it was surprisingly found that a flexible conduit could be provided which confers improved mechanical strength, for example improved axial tensile strength, while still being permeable to water vapor and one or more further breathing gases such as carbon dioxide.

In a further aspect of the invention there is provided a flexible conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall is permeable to water vapor and one or more further breathing gases, such as carbon dioxide.

As used herein, "axial tensile strength" means the amount of axial pull force the enclosing wall of a conduit can withstand until breakage occurs. Methods to determine the tensile strength of a conduit are known in the art. A suitable method to determine the tensile strength is by mounting a piece of xx cm, typically 10-15 cm, preferably 15 cm of the conduit between two clamps at room temperature, slowly (e.g. at a speed of 50 mm/min or less) stretching the tube in the axial direction and using a Mecmesin PFI 200 force gauge to determine the amount of force applied when breakage occurs, wherein breakage can be observed visually and/or by a drop in the force measured. All values for the axial tensile strength provided herein refer to the axial tensile strength as determined by this method.

As explained above, it was surprisingly found that it would be desirable if a conduit was provided which allows the removal of liquid water from the flow passage of the conduit, at least to some extent.

In a further aspect of the invention there is thus provided a flexible conduit for a breathing circuit as defined herein above wherein said enclosing wall is characterized by a liquid water removal rate of more than 0.0001 $g/(cm^{2}*hour)$, preferably more than 0.0005 $g/(cm^{2}*hour)$, preferably more than 0.001 $g/(cm^{2}*hour)$, preferably more than more than 0.005 $g/(cm^{2}*hour)$, which may be tested in accordance with the liquid water test procedure.

The present inventors also found that a flexible conduit in accordance with the invention can be advantageously produced by a highly efficient helical winding process, resulting in a helically wound conduit. The flexible conduit wall may thus be made out of a plurality of laterally connected windings of a helically wound or wrapped strip, or web, or multiple strips or webs, wherein the adjacent windings of the strip(s) or web(s) are attached to each other by means of a weld or welds.

In a further aspect of the invention there is thus provided a flexible conduit for a breathing circuit as defined herein above wherein the enclosing wall comprises a first helically wrapped web.

The flexible conduit of the present invention is advantageously incorporated in a limb for a breathing circuit, in particular the inspiratory or expiratory limb. In a fifth aspect there is provided a limb for a breathing circuit comprising at least one conduit according to the invention, a first connector mounted at a first end of the at least one conduit and a second connector mounted at a second end of the at least one conduit, wherein the first connector is provided for connecting to a first device of the breathing circuit, for example a patient interface, and the second connector is provided for connecting to a second device of the breathing circuit, for example a humidifier, a ventilator or other device.

In a further aspect of the invention there is provided a method of producing a flexible conduit, comprising:

a) providing at least a first polymer material or blend,
c) extruding at least one rib,
d) extruding at least one web, and
e) forming said conduit by helically winding said at least one web and joining adjacent windings of said at least one web by means of said at least one rib, wherein said first polymer material or blend is used for at least a first web among said at least one web and is a predetermined material or blend, selected for making said first web permeable to water vapor and one or more further breathing gases.

In embodiments, the predetermined material or blend may be selected from the group of Kraton D2104, Kraton D1101, Kraton G1652, Kraton G2705, Estane 58245, Estane MVT (such as MVT 90 NT1, MVT 80 NT1 or MVT 75AT3) Pebax MV 3000 SP 01, Arnitel VT (such as VT3108, VT3118 or VT 7812), Pebax MV6100, Butadiene TPE, Nylon 66, Cyclolac 1033, Hytrel 5556, PET, PVDF, EAA, PP, FEP, LCP, TPU (e.g. polyether TPU) and PTFE, preferably Arnitel VT3108. In preferred embodiments, the predetermined material is selected from one or more of the following commercially available material brands: Hytrel, Arnitel. In more preferred embodiments the predetermined material is one or more of the following commercially available materials: Arnitel VT3108, Arnitel VT3118, Arnitel VT7812 and Arnitel VT3104, preferably one or more of Arnitel VT3108 and Arnitel VT3104, most preferably Arnitel VT3108.

The present inventors have surprisingly found that the conduit in accordance with the invention at least to some extent may extend the life of the $CO_2$ scrubbers in a breathing apparatus and/or reduce the amount of water generated by a $CO_2$ scrubber.

In a further aspect of the invention there is provided a method of circulating breathing gases of a patient comprising:
  providing a limb for a breathing circuit comprising at least one conduit according to the invention, a first connector mounted at the first end of the at least one conduit and a second connector mounted at the second end of the at least one conduit, wherein the first connector is connected to a patient interface and the second connector is connected to a closed-system breathing apparatus comprising a $CO_2$ scrubber;
  circulating breathing gases through the closed-system breathing apparatus; and
  transmitting at least some $CO_2$ from said breathing gases through the enclosing wall of said conduit.

BRIEF DESCRIPTION OF THE FIGURES

FIG. 8A shows a conduit in accordance with the invention 12 partitioned into a first flow passage 13 and a second flow passage 14. FIG. 8B shows a conduit in accordance with the invention 12 partitioned into a first flow passage 13, a second flow passage 14 and a third flow passage 15.

DETAILED DESCRIPTION OF THE INVENTION

Figure 1:
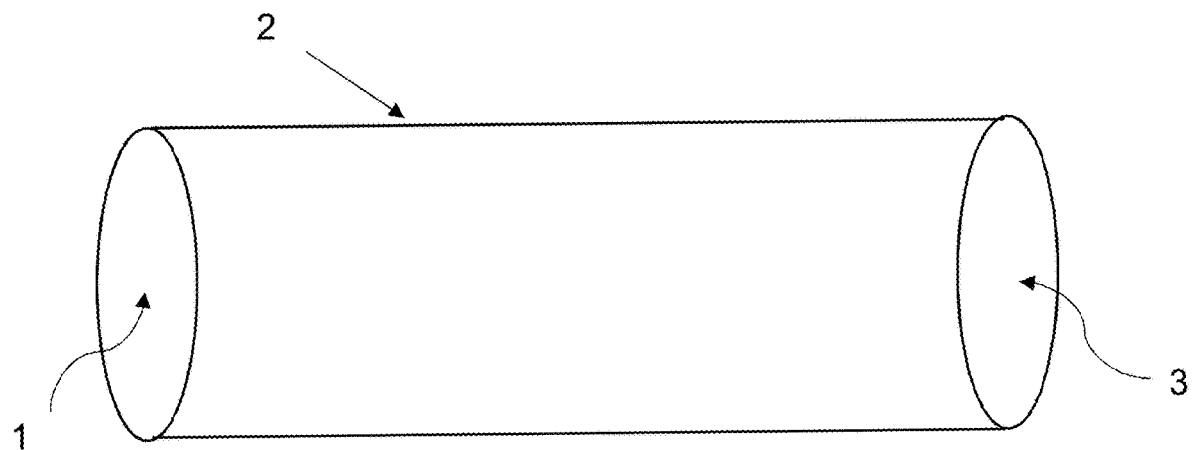
FIG. 1 shows a conduit according to the invention comprising an inlet 1, an enclosing wall 2 which allows the passage of water vapor and one or more further breathing gases as defined herein elsewhere and an outlet 3.

Hereafter, the present invention will be described by means of specific embodiments and with reference to certain drawings, yet the invention is not limited thereto and will only be defined by the claims. The drawings provided here are merely schematic representations and are not limiting. In the drawings, dimensions of certain parts can be shown enlarged, which means that the parts involved are not depicted on scale, and this merely for illustrative purposes. The dimensions and the relative dimensions do not necessarily correspond with the practical embodiments of the invention.

Furthermore, certain terms such as "first", "second", "third" and the like will be used in the description and claims to make a distinction between similar elements and are not necessarily meant to indicate a sequential or chronological order. The terms in question are interchangeable in the conditions appropriate therefore, and the embodiments of the invention may work in other sequences than those that are illustrated or described here.

Furthermore, terms such as "top", "bottom", "above", "under", and the like in the description and in the claims are used for descriptive purposes and not necessarily to indicate relative positions. The said terms used are interchangeable in the conditions appropriate therefore, and the embodiments of the invention may work in other orientations than described or illustrated here.

The term "comprising" and derivative terms, as they are used in the claims, should not be interpreted as limited to the means that are mentioned thereafter; the term does not exclude other elements or steps. The term should be interpreted as a specification of the mentioned properties, integers, steps, or components that are referred to, without excluding the presence or the addition of additional properties, integers, steps, or components, or groups thereof. The scope of an expression such as "a device comprising means A and B" is therefore not only restricted to devices that merely consist of components A and B. On the other hand, what is meant is that, as far as the present invention is concerned, the only relevant components are A and B.

Furthermore, the expressions "at least one" and "one or more" are used interchangeably.

What is referred to by use herein of the terms "welded", "bonded", "heat-bonded", "welding", "bonding" and "heat-bonding" is a joining together, in a heated environment or as a result of an application of heat energy (whether applied by radiation, convection, the use of laser-generated light or any other known or yet to be developed technique, or a combination thereof) of rubber or thermoplastic materials from which components of the conduit may be formed. This results in or amounts to an integral assembly that typically exhibits no remaining borders between adjacent portions of the bonded or welded materials. In essence, the terms "welded", "bonded", and "heat-bonded" and the terms "welding", "bonding" and "heat-bonding" are used interchangeably, with no differences of meaning intended there between.

The terms "permeability", "permeation", "permeable to", "allows the passage of", "transmission" their conjugations and variants as used herein with reference to the characteristics of the enclosing wall are used interchangeably and should not be construed as limiting with regards to a specific mechanism or physical and/or chemical process. Appropriate test methods are described throughout this document.

The term 'flexible' as used herein means that the conduit can be bent around (while remaining in contact with) a half circumference of a 2.5 cm metal pipe and exhibit a pressure drop of less than 150% of the pressure drop of the conduit when it is straight. A suitable test method is in accordance with ISO5367.

In accordance with the invention there is provided a flexible conduit for a breathing circuit comprising an inlet, an outlet, and an enclosing wall defining a flow passage between said inlet and said outlet wherein the enclosing wall is permeable to water vapor and one or more further breathing gases. In embodiments, the one or more further breathing gases is selected from the group consisting of $O_2$ and/or $CO_2$, for example $CO_2$. In embodiments, the enclosing wall is sufficiently permeable to water vapor such that condensation is substantially reduced or avoided during normal use an exhalation limb in a breathing circuit compared to a non-permeable/breathable limb known in the art.

In an aspect of the invention there is thus provided a flexible conduit for a breathing circuit comprising an inlet, an outlet, and an enclosing wall defining a flow passage between said inlet and said outlet wherein the enclosing wall is permeable to water vapor and one or more of $O_2$ and $CO_2$, preferably the enclosing wall is permeable to water vapor and $CO_2$. In embodiments, the enclosing wall is sufficiently permeable to $CO_2$ such that the operation time of a $CO_2$ scrubber before needing regeneration is increased by at least 1%, for example at least 5% compared to a limb known in the art which is not permeable to $CO_2$.

In accordance with embodiments of the invention there is provided a flexible conduit for a breathing circuit comprising an inlet, an outlet, and an enclosing wall defining a flow passage between said inlet and said outlet, wherein at least a region of said enclosing wall is permeable to water vapor and one or more of $O_2$ and $CO_2$, preferably at least a region of said enclosing wall is permeable to water vapor and $CO_2$.

The water vapor transmission rate (WVTR) of a conduit may be determined in accordance with the following procedure, herein referred to as "WVTR test procedure": The water vapor transmission rate of is tested at an ambient temperature of 23° C. and an ambient humidity of 35% RH. Compressed air of <5% RH is humidified by a humidifier mounted before the conduit to approximately 100% RH and fed via a splitter to the conduit and a 'non-breathable' control conduit (such as metallocene PE) at a rate of 7.5 liter per minute (for each conduit) for 24 hours. The conduit to be tested is heated at 18 Watt. After passing through the conduits, the air from each conduit is led to a water trap and the amount of water collected in the trap over 24 hours determined based on the weight of the trap before the experiment and after 24 hours. The WVTR is calculated based on the difference between the amount of water collected by the water traps associated to the non-breathable control and the conduit to be tested respectively.

The permeability of the enclosing wall or a region thereof to water vapor may be characterized by a water vapor transmission rate of at least 0.01 g/(cm²*day), preferably at least 0.05 g/(cm²*day), or at least 0.1 g/(cm²*day), which may be tested in accordance with the WVTR test procedure.

In embodiments the enclosing wall is sufficiently permeable to water vapor such that it is capable of reducing the relative humidity of a gas stream, determined at the inlet and the outlet of the conduit, by more than 5%, preferably by more than 10%, preferably by more than 20%, for example when used as the expiratory limb in a breathing apparatus. In embodiments the enclosing wall is sufficiently permeable to water vapor such that it is capable of removing more than 1 g, preferably more than 10 g, preferably more than 50 g of water from a gas stream, determined over 24 hours, for example when used as the expiratory limb in a breathing apparatus The $O_2$ transmission rate of a conduit may be determined in accordance with the following procedure, herein referred to as "$O_2$ test procedure": The $O_2$ transmission rate is determined at 38° C. using the system MOCON OX-TRAN 2/21 MH by cutting the conduit to a piece of 10 cm length and closing the inlet and the outlet of the resulting 10 cm conduit by gluing each of the inlet and the outlet to a metal plate using epoxy glue. One of the metal plates is mounted with tubing to allow flushing the flow passage of the conduit with carrier gas ($N_2/H_2$). The relative humidity of the carrier gas is approximately 86%. The conduit is placed in a glass chamber which is flushed with 1% Oxygen (in $N_2$) and the Oxygen Transmission Rate from the glass chamber into the conduit is determined using a coloux sensor which analyzes the carrier gas. The gas flow is set low such that the experiment is performed at barometric pressure on both sides of the sample The $CO_2$ transmission rate of a conduit may be determined in accordance with the following procedure, herein referred to as "$CO_2$ test procedure": The $CO_2$ transmission rate is determined at 38° C. using the system MOCON PERMATRAN-C 4/41 by cutting the conduit to a piece of 10 cm length and closing the inlet and the outlet of the resulting 10 cm conduit by gluing each of the inlet and the outlet to a metal plate using epoxy glue. One of the metal plates is mounted with tubing to allow flushing the flow passage of the conduit with carrier gas ($N_2/H_2$). The carrier gas is dry (relative humidity approximately 0%). The conduit was placed in a glass chamber which was flushed with 4% carbon dioxide (in $N_2$) and the Carbon Dioxide Transmission Rate from the glass chamber into the conduit is determined using a coloux sensor which analyzes the carrier gas. The gas flow is set low such that the experiment is performed at barometric pressure on both sides of the sample The permeability of the enclosing wall or a region thereof to $CO_2$ may be characterized by a $CO_2$ transmission rate of more than 1 $cm^3/(m^2*day*bar)$, preferably more than 10 $cm^3/(m^2*day*bar)$, more than 100 $cm^3/(m^2*day*bar)$, more than 300 $cm^3/(m^2*day*bar)$ or more than 370 $cm^3/(m^2*day*bar)$, which may be tested in accordance with the $CO_2$ test procedure. The permeability of the enclosing wall or a region thereof to $CO_2$ may be characterized by a $CO_2$ transmission rate of less than 100000 $cm^3/(m^2*day*bar)$, preferably less than 10000 $cm^3/(m^2*day*bar)$, less than 1000 $cm^3/(m^2*day*bar)$, less than 500 $cm^3/(m^2*day*bar)$ or less than 420 $cm^3/(m^2*day*bar)$ which may be tested in accordance with the $CO_2$ test procedure.

In embodiments the enclosing wall is sufficiently permeable to water vapor such that it is capable of reducing the $CO_2$ content of a gas stream, determined at the inlet and the outlet of the conduit, wherein said reduction is more than 0.1%, such as more than 1%, more than 5% or more than 10%. In embodiments said reduction is less than 80%, such as less than 50%, less than 40% or less than 20%.

The permeability of the enclosing wall or a region thereof to $O_2$ may be characterized by an $O_2$ transmission rate of more than 0.1 $cm^3/(m^2*day*bar)$, preferably more than 1 $cm^3/(m^2*day*bar)$, more than 10 $cm^3/(m^2*day*bar)$ or more than 20 $cm^3/(m^2*day*bar)$ which may be tested in accordance with the $O_2$ test procedure. The permeability of the enclosing wall or a region thereof to $O_2$ may be characterized by an $O_2$ transmission rate of less than 10000 $cm^3/(m^2*day*bar)$, preferably less than 1000 $cm^3/(m^2*day*bar)$, less than 100 $cm^3/(m^2*day*bar)$, less than 50 $cm^3/(m^2*day*bar)$ or less than 30 $cm^3/(m^2*day*bar)$ which may be tested in accordance with the $O_2$ test procedure.

FIG. 1 shows a conduit according to the invention comprising an inlet 1, an enclosing wall 2 which allows the passage of water vapor and one or more further breathing gases as defined herein before and an outlet 3.

In accordance with the invention there is provided a flexible conduit for a breathing circuit comprising an inlet, an outlet, and an enclosing wall defining a flow passage between said inlet and said outlet, wherein said enclosing wall has high mechanical strength and wherein the enclosing wall still allows the passage of water vapor and one or more further breathing gases.

The mechanical strength of the enclosing wall 2 may be assessed by standardized tests known to the person skilled in the art. In preferred embodiments, a conduit as defined herein above is provided wherein the axial tensile strength of the enclosing wall is greater than 40N preferably greater than 50N, greater than 65N, greater than 80N, greater than 95N or greater than 110N. In highly preferred embodiments the axial tensile strength is inherent to the construction of the enclosing wall as such, and no reinforcing measures, such as for example longitudinal reinforcement threads or other means for pull-relief, are applied.

In accordance with a preferred embodiment of the invention there is thus provided a conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall is characterized by a water vapor transmission rate of at least 0.01 $g/(cm^2*day)$, preferably at least 0.05 $g/(cm^2*day)$, or at least 0.1 $g/(cm^2*day)$, which may be tested in accordance with the WVTR test procedure; and a $CO_2$ transmission rate of more than 1 $cm^3/(m^2*day*bar)$, preferably more than 10 $cm^3/(m^2*day*bar)$, more than 100 $cm^3/(m^2*day*bar)$, more than 300 $cm^3/(m^2*day*bar)$ or more than 370 $cm^3/(m^2*day*bar)$ which may be tested in accordance with the $CO_2$ test procedure.

In accordance with a preferred embodiment of the invention there is thus provided a conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall is characterized by a water vapor transmission rate of at least 0.01 $g/(cm^2*day)$, preferably at least 0.05 $g/(cm^2*day)$, or at least 0.1 $g/(cm^2*day)$, which may be tested in accordance with the WVTR test procedure; a $CO_2$ transmission rate of more than 1 $cm^3/(m^2*day*bar)$, preferably more than 10 $cm^3/(m^2*day*bar)$, more than 100 $cm^3/(m^2*day*bar)$, more than 300 $cm^3/(m^2*day*bar)$ or more than 370 $cm^3/(m^2*day*bar)$ which may be tested in accordance with the $CO_2$ test procedure, and a $CO_2$ transmission rate of less than 100000 $cm^3/(m^2*day*bar)$, preferably less than 10000 $cm^3/(m^2*day*bar)$, less than 1000 $cm^3/(m^2*day*bar)$, less than 500 $cm^3/(m^2*day*bar)$ or less than 420 $cm^3/(m^2*day*bar)$ which may be tested in accordance with the $CO_2$ test procedure.

In accordance with a preferred embodiment of the invention there is thus provided a conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall is characterized by a water vapor transmission rate of at least 0.01 $g/(cm^2*day)$, preferably at least 0.05 $g/(cm^2*day)$, or at least 0.1 $g/(cm^2*day)$, which may be tested in accordance with the WVTR test procedure; a $CO_2$ transmission rate of more than 1 $cm^3/(m^2*day*bar)$, preferably more than 10 $cm^3/(m^2*day*bar)$, more than 100 $cm^3/(m^2*day*bar)$, more than 300 $cm^3/(m^2*day*bar)$ or more than 370 $cm^3/(m^2*day*bar)$ which may be tested in accordance with the $CO_2$ test procedure, and an $O_2$ transmission rate of more than 0.1 $cm^3/(m^2*day*bar)$, preferably more than 1 $cm^3/(m^2*day*bar)$, more than 10 $cm^3/(m^2*day*bar)$ or more than 20 $cm^3/(m^2*day*bar)$ which may be tested in accordance with the $O_2$ test procedure.

In accordance with embodiments of the invention, the enclosing wall is permeable to liquid water.

The liquid water removal rate of a conduit may be determined in accordance with the following procedure, herein referred to as "liquid water test procedure": The liquid water removal rate is tested in a climate controlled room at 22° C. and 35% RH and the conduit is preconditioned in this room for 12 hours preceding the test. The weight of the conduit is recorded and the conduit is suspended in a "u" shape using clamps such that the inlet and outlet of the conduit were at the same height and facing upwards relative to the floor. Next, the conduit is filled with water, the inlet and outlet is closed with parafilm (a material with low water permeability) and the liquid water removal rate is monitored by recording the water level relative to the starting level every hour. After eight hours, the test is stopped and the weight of the conduit and of the remaining water was recorded. The liquid water removal rate is averaged over 8 hours and calculated using the inner surface area of the tube which was in contact with liquid water at the beginning of the test.

Thus, in preferred embodiments, a conduit is provided wherein said enclosing wall is characterized by a liquid water removal rate of more than 0.0001 g/(cm²*hour), preferably more than 0.0005 g/(cm²*hour), preferably more than 0.001 g/(cm²*hour), preferably more than more than 0.005 g/(cm²*hour), which may be tested in accordance with the liquid water test procedure.

In accordance with a preferred embodiment of the invention there is thus provided a conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall, or at least a region thereof, is permeable to water vapor and one or more further breathing gases and is characterized by a liquid water removal rate of more than 0.0001 g/(cm²*hour), preferably more than 0.0005 g/(cm²*hour), preferably more than 0.001 g/(cm²*hour), preferably more than more than 0.005 g/(cm²*hour), which may be tested in accordance with the liquid water test procedure.

In accordance with a preferred embodiment of the invention there is thus provided a conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall is characterized by a water vapor transmission rate of at least 0.01 g/(cm²*day), preferably at least 0.05 g/(cm²*day), or at least 0.1 g/(cm²*day), which may be tested in accordance with the WVTR test procedure; a $CO_2$ transmission rate of more than 1 cm³/(m²*day*bar), preferably more than 10 cm³/(m²*day*bar), more than 100 cm³/(m²*day*bar), more than 300 cm³/(m²*day*bar) or more than 370 cm³/(m²*day*bar) which may be tested in accordance with the $CO_2$ test procedure; and a liquid water removal rate of more than 0.0001 g/(cm²*hour), preferably more than 0.0005 g/(cm²*hour), preferably more than 0.001 g/(cm²*hour), preferably more than more than 0.005 g/(cm²*hour), which may be tested in accordance with the liquid water test procedure.

In accordance with a preferred embodiment of the invention there is thus provided a conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall is characterized by a water vapor transmission rate of at least 0.01 g/(cm²*day), preferably at least 0.05 g/(cm²*day), or at least 0.1 g/(cm²*day), which may be tested in accordance with the WVTR test procedure; a $CO_2$ transmission rate of more than 1 cm³/(m²*day*bar), preferably more than 10 cm³/(m²*day*bar), more than 100 cm³/(m²*day*bar), more than 300 cm³/(m²*day*bar) or more than 370 cm³/(m²*day*bar) which may be tested in accordance with the $CO_2$ test procedure; a $CO_2$ transmission rate of less than 100000 cm³/(m²*day*bar), preferably less than 10000 cm³/(m²*day*bar), less than 1000 cm³/(m²*day*bar), less than 500 cm³/(m²*day*bar) or less than 420 cm³/(m²*day*bar) which may be tested in accordance with the $CO_2$ test procedure; and a liquid water removal rate of more than 0.0001 g/(cm²*hour), preferably more than 0.0005 g/(cm²*hour), preferably more than 0.001 g/(cm²*hour), preferably more than more than 0.005 g/(cm²*hour), which may be tested in accordance with the liquid water test procedure.

In accordance with a preferred embodiment of the invention there is thus provided a conduit for a breathing circuit comprising an inlet, an outlet, and an enclosing wall defining a flow passage between said inlet and said outlet, wherein the axial tensile strength of said enclosing wall is greater than 40N preferably greater than 50N, greater than 65N, greater than 80N, greater than 95N or greater than 110N and wherein the enclosing wall is characterized by a water vapor transmission rate of at least 0.01 g/(cm²*day), preferably at least 0.05 g/(cm²*day), or at least 0.1 g/(cm²*day), which may be tested in accordance with the WVTR test procedure; a $CO_2$ transmission rate of more than 1 cm³/(m²*day*bar), preferably more than 10 cm³/(m²*day*bar), more than 100 cm³/(m²*day*bar), more than 300 cm³/(m²*day*bar) or more than 370 cm³/(m²*day*bar) which may be tested in accordance with the $CO_2$ test procedure; an $O_2$ transmission rate of more than 0.1 cm³/(m²*day*bar), preferably more than 1 cm³/(m²*day*bar), more than 10 cm³/(m²*day*bar) or more than 20 cm³/(m²*day*bar) which may be tested in accordance with the $O_2$ test procedure; and a liquid water removal rate of more than 0.0001 g/(cm²*hour), preferably more than 0.0005 g/(cm²*hour), preferably more than 0.001 g/(cm²*hour), preferably more than more than 0.005 g/(cm²*hour), which may be tested in accordance with the liquid water test procedure.

In preferred embodiments, the enclosing wall is not pierced, e.g. as the result of mechanical perforation or piercing of the material of which the enclosing wall is produced during the production process of the conduit of the invention.

In preferred embodiments, the web and/or rib, preferably the web region of the enclosing wall is monolithic with respect to water vapor, $CO_2$ and/or $O_2$ permeability.

The present inventors have surprisingly found that it is possible to produce a conduit possessing the mechanical properties and permeation properties described above which also possess desirable optical properties. Low haze tubes are not only relevant from an esthetical perspective but are also preferred as they provide the possibility of visual inspection for condensation of water vapor or for accumulation of bodily fluids excreted by the patient such as blood, phlegm etc.

In accordance with embodiments of the invention, the enclosing wall of the conduit comprises a region which allows inspection of the contents of the conduit. In embodiments said region has low haze. In embodiments said region is characterized by a haze of less than 30%, preferably less than 20%, preferably less than 10%, preferably less than 4% as may be determined in accordance with ASTM D1003.

In embodiments the conduit comprises more than 5% weight, preferably more than 15% by weight of said low haze region.

In accordance with embodiments of the invention, the enclosing wall of the conduit comprises, or consists of a thermoplastic elastomer, preferably a copolyester, preferably a hydrophilic polyester block copolymer, preferably a polybutyleneterephtalate block copolyester.

In embodiments the enclosing wall of the conduit comprises, or consists of a polymer selected from the group consisting of polyethyleneterephtalate esters (PET), polybutyleneterephtalate esters (PBT), polyvinylidene fluorides (PVDF), ethylene acrylic acid copolymers (EAA), polypropylenes (PP), fluorinated ethylene propylene copolymers (FEP), liquid crystal polymers (LCP), polytetrafluoroethylenes (PTFE) and polybutyleneterephtalate block copolyesters, preferably polybutyleneterephtalate block copolyesters.

In embodiments, the enclosing wall of the conduit comprises or consists of a polymer selected from one or more of the following commercially available materials: Kraton D2104, Kraton D1101, Kraton G1652, Kraton G2705, Estane 58245, Estane MVT (such as MVT 90 NT1, MVT 80 NT1 or MVT 75AT3), Pebax MV 3000 SP 01, Arnitel VT (such as VT3108, VT3118 or VT 7812), Pebax MV6100, Nylon 66, Cyclolac 1033 and Hytrel 5556, preferably Arnitel VT3108, Arnitel VT3118, Arnitel VT7812 and Arnitel VT3104, preferably Arnitel VT3108 and Arnitel VT3104, most preferably Arnitel VT3108.

Figure 2:
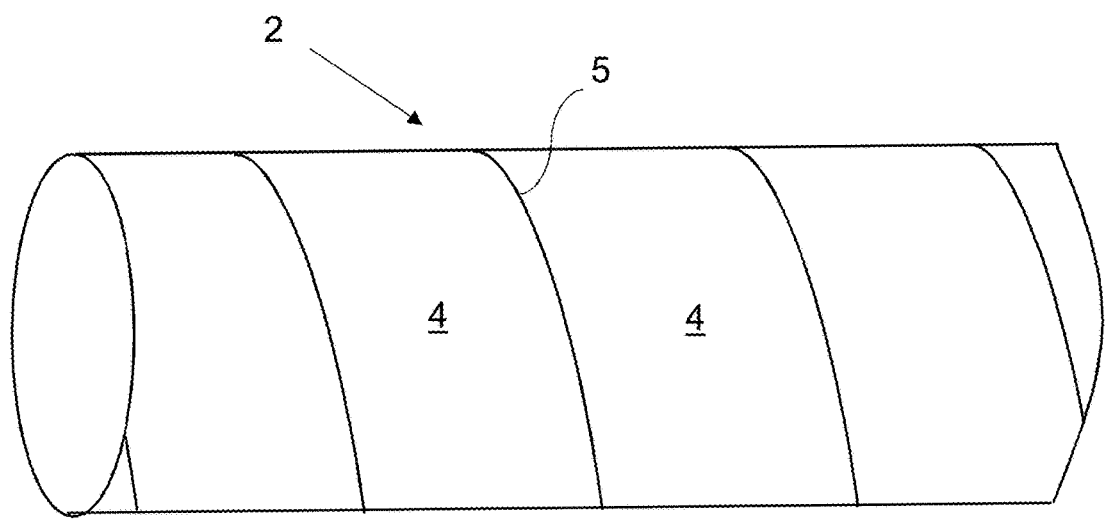
FIG. 2 shows an enclosing wall 2 comprising a plurality of laterally connected windings of a helically wound or wrapped strip, which is the first web 4, wherein the adjacent windings of the web are attached to each at the interface 5.
Figure 3:
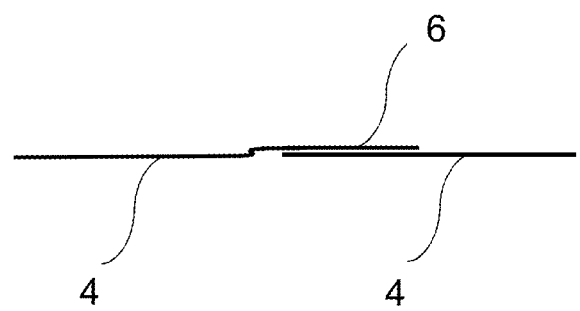
FIG. 3 shows a simple weld 6 which is the result of heat-bonding of overlapping areas of the web material of adjacent turns of the first web 4.
Figure 4:
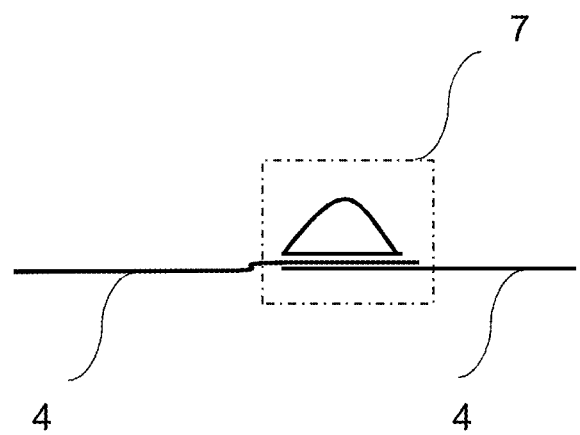
FIGS. 4A and 4B shows a helically wound rib 7 heat-bonded to adjacent turns of a helically wound first web 4.
Figure 4:
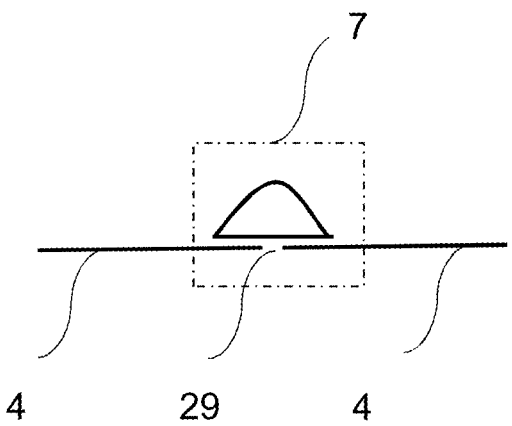

In preferred embodiments, the conduit in accordance with the invention is a helically wound conduit. Thus, in embodiments according to the invention, the enclosing wall of the flexible conduit comprises a first helically wrapped web comprising or consisting of a first web material. FIG. 2 shows an enclosing wall 2 comprising a plurality of laterally connected windings of a helically wound or wrapped strip, which is the first web 4, wherein the adjacent windings of the web are attached to each at the interface 5. As used herein, the interface 5 is to be construed broadly and comprises any means of uniting two adjacent windings of the first web to into an integral assembly. This may comprise a simple weld 6 which is the result of heat-bonding of overlapping areas of the web material of adjacent turns of the first web 4 as shown in FIG. 3. Alternatively, this may comprise more elaborate structures as described below. The interface 5 may thus constitute a reinforcing rib structure. The interface 5 may comprise other materials than the first web material. The general principle of introducing a rib part alternating with a web part to confer flexibility and strength are known to the skilled person and require no further explanation. In preferred embodiments a conduit as described herein is thus provided wherein said enclosing wall comprises a first helical web and a first helically wound rib 7 and wherein the rib is heat-bonded to adjacent turns of said first helical web 4. An embodiment is shown in FIG. 4B, wherein the adjacent turns of the web are separated by a space 29, while FIG. 4A shows an embodiment wherein adjacent turns of the web are adjoining or overlapping. In preferred embodiments the adjacent turns of the web are not adjoining or overlapping and are separated by a space 29.

In preferred embodiments the first web material comprises, or consists of a thermoplastic elastomer, preferably a copolyester, preferably a hydrophilic polyester block copolymer, preferably a polybutyleneterephtalate block copolyester.

In embodiments the first web material comprises, or consists of a polymer selected from the group consisting of polyethyleneterephtalate esters (PET), polybutyleneterephtalate esters (PBT), polyvinylidene fluorides (PVDF), ethylene acrylic acid copolymers (EAA), polypropylenes (PP), fluorinated ethylene propylene copolymers (FEP), liquid crystal polymers (LCP), polytetrafluoroethylenes (PTFE), TPU (e.g. polyether TPU) and polybutyleneterephtalate block copolyesters, preferably polybutyleneterephtalate block copolyesters.

In embodiments, the first web material comprises or consists of a polymer selected from one or more of the following commercially available materials: Kraton D2104, Kraton D1101, Kraton G1652, Kraton G2705, Estane 58245, Estane MVT (such as MVT 90 NT1, MVT 80 NT1 or MVT 75AT3), Pebax MV 3000 SP 01, Arnitel VT (such as VT3108, VT3118 or VT 7812), Pebax MV6100, Nylon 66, Cyclolac 1033 and Hytrel 5556, preferably Arnitel VT3108, Arnitel VT3118, Arnitel VT7812 and Arnitel VT3104, preferably Arnitel VT3108 and Arnitel VT3104, most preferably Arnitel VT3108. In preferred embodiments, the first web material comprises or consists of a polymer selected from one or more of the following commercially available material brands: Hytrel, Arnitel. In more preferred embodiments the first web material comprises or consists of a polymer selected from one or more of the following commercially available materials: Arnitel VT3108, Arnitel VT3118, Arnitel VT7812 and Arnitel VT3104, preferably one or more of Arnitel VT3108 and Arnitel VT3104, most preferably Arnitel VT3108.

In embodiments the first web may be a polymeric foam, preferably a closed-cell foam.

In highly preferred embodiments, the web has low haze. In embodiments the web is characterized by a haze of less than 30%, preferably less than 20%, preferably less than 10%, preferably less than 4% as may be determined in accordance with ASTM D1003.

In embodiments the first rib material comprises, or consists of a polymer selected from the group consisting of polyethyleneterephtalate esters (PET), polybutyleneterephtalate esters (PBT), polyvinylidene fluorides (PVDF), ethylene acrylic acid copolymers (EAA), polypropylenes (PP), fluorinated ethylene propylene copolymers (FEP), liquid crystal polymers (LCP), polytetrafluoroethylenes (PTFE) and polybutyleneterephtalate block copolyesters, preferably selected from polybutyleneterephtalate block copolyesters and polypropylene.

In embodiments, the first rib material comprises or consists of a polymer selected from one or more of the following commercially available materials: Kraton D2104, Kraton D1101, Kraton G1652, Kraton G2705, Estane 58245, Estane MVT (such as MVT 90 NT1, MVT 80 NT1 or MVT 75AT3), Pebax MV 3000 SP 01, Arnitel VT (such as VT3108, VT3118 or VT 7812), Pebax MV6100, Nylon 66, Cyclolac 1033 and Hytrel 5556, preferably Arnitel VT3108, Arnitel VT3118, Arnitel VT7812 and Arnitel VT3104, preferably Arnitel VT3108 and Arnitel VT3104, most preferably Arnitel VT3108. In preferred embodiments, the first rib material comprises or consists of a polymer selected from one or more of the following commercially available material brands: Hytrel, Arnitel. In more preferred embodiments the first rib material comprises or consists of a polymer selected from one or more of the following commercially available materials: Arnitel VT3108, Arnitel VT3118, Arnitel VT7812 and Arnitel VT3104, preferably one or more of Arnitel VT3108 and Arnitel VT3104, most preferably Arnitel VT3108.

Figure 5:
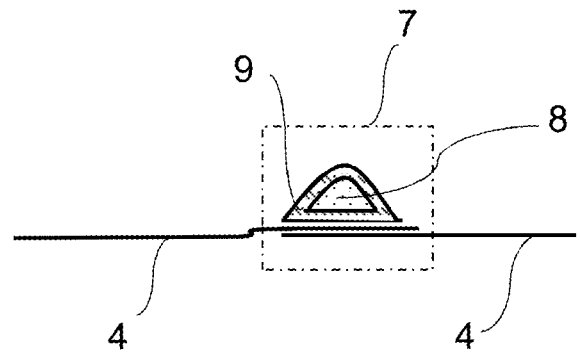
FIGS. 5A and 5B show a helically wound rib 7 heat-bonded to adjacent turns of a first helical web 4 wherein the rib comprises a first inner polymer material 8, embedded in a second outer polymer material 9 different from said first inner polymer material.
Figure 5:
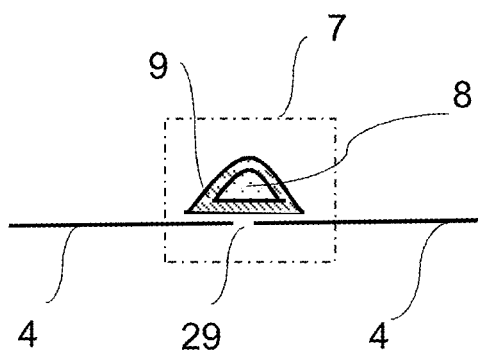
Figure 6:
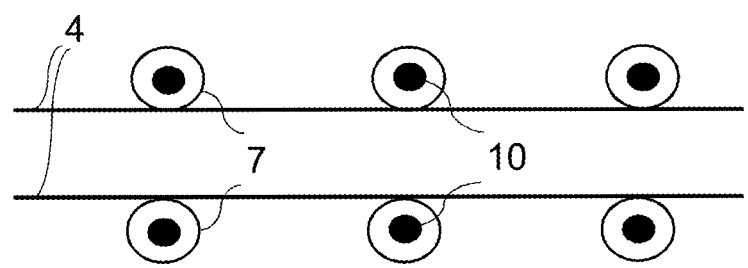
FIGS. 6A, 6B and 6C show a cross-sectional view of a part of the enclosing wall in axial direction of the conduit in accordance with the invention comprising a helically wound first web 4 and a helically wound rib 7 and demonstrate a number of possible arrangements for one or more electrically conductive wires 10.
Figure 6:
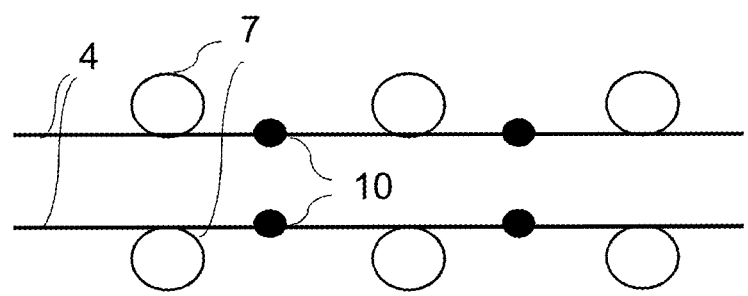
Figure 6:
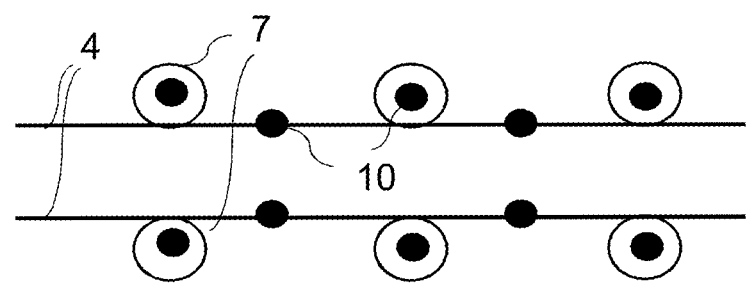

In embodiments, as shown in FIGS. 5A and 5B the first rib comprises a first inner polymer material 8, partially embedded, preferably embedded in a second outer polymer material 9 different from said first inner polymer material. It is preferred that the first inner polymer material comprises polypropylene and the second outer polymer material comprises a polybutyleneterephtalate block copolyester such as Arnitel VT3108 or Arnitel VT3104, preferably Arnitel VT3108. In highly preferred embodiments, the second outer polymer material 9 is a blend of the first inner polymer material 8 and the first web material, for example a blend of a ratio within the range of 20:80 to 80:20, preferably within the range of 30:70 to 70:30. The first helical rib may be located at the outside of the conduit, i.e. at the convex side of the enclosing wall or at the inside of the conduit, i.e. at the concave side of the enclosing wall.

In an embodiment, a flexible conduit in accordance with the invention comprises a helically wound profile having the shape such as for example disclosed in international patent application WO 2011/051870 A1, FIGS. 3, 4, 7, 8, 9, 10, 12, 13, 15, 16, 17 and 19 and corresponding sections of the description of said application, which are herewith incorporated by reference in the current application.

In an embodiment, a helically wound flexible conduit in accordance with the invention comprises a profile such as for example disclosed in U.S. Pat. No. 9,230,712 B2, FIGS. 1-17 and corresponding sections of the description of said patent, which are herewith incorporated by reference in the current application.

In an embodiment, a profile of the invention is made by co-extruding an outer profile facing one side of the profile, and an inner profile, facing the opposite side of the profile, such that when the profile is for example wound into a helically wound hose, the outer profile is facing the exterior of the flexible hose and the inner profile is facing the inside of the hose.

Alternatively, a profile of the invention is made at least in part from one or more co-extrusion parts. For example, the bottom or web of a profile of the invention may be made of a relatively flexible material and the remaining part of the profile may be made of a different more stiff material.

In one embodiment, a flexible conduit in accordance with the invention comprising a profile which ends on both sides in an upright part is provided. The weld is located between the upright part of the adjacent windings and together with these upright parts forms a helical reinforcement rib on the flexible wall of the conduit, such as for example disclosed in FIGS. 14-16 of U.S. Pat. No. 9,230,712 B2, and corresponding section of the description, which are incorporated by reference.

In one embodiment, a flexible conduit in accordance with the invention is provided which is stretchable, comprising an unfoldable, or expandable part that is provided to be unfolded when an axial tensile force is exerted onto the hose, such as to provide for an elongation of the hose or wherein the web part comprises a collapsible part. In preferred embodiments the stretchable conduit of the invention provides the advantageous properties described above such as but not limited to, water vapor and breathing gases permeability in its elongated state.

In preferred embodiments a flexible conduit in accordance with the invention comprises a helically wound profile as shown in FIG. 15D. This profile comprises a first extruded rib part 25 between two non-overlapping adjacent windings of the first web 4. The first extruded rib part 25 has at least one valley shaped area 26, for example 2 valley shaped areas 26, which accommodates at least one electrically conductive wire 10 (e.g. for heating purposes). The profile comprises a second rib part 27 which covers the at least one electrically conductive wire 10. The helically wound profile as shown in FIG. 15D has several advantages, such as increased manufacturing efficiency due to easy and reproducible wire placement and easier automatisation of subsequent manufacturing steps since the transition or 'seam' between the first rib part 25 and the second rib part 27 allows easy access to the at least one electrically conductive wire 10, for example to attach an interface.

In embodiments the conduit is an inspiratory conduit. In embodiments the conduit is an expiratory conduit. In embodiments the same conduit can function as an inspiratory or expiratory conduit.

In order to function optimally in applications such as a breathing circuit, it is preferred that the flexible conduit of the invention comprises one or more heating means, such as but not limited to electrically conductive wires, printed electronics, printed inks, positive temperature coefficient of resistance (PTC) materials, negative temperature coefficient of resistance (NTC) materials etc.

In preferred embodiments, the flexible conduit of the invention comprises one or more electrically conductive wires provided for heating, transferring sensor signals or a combination thereof. For example, the conduit may comprise one, two, three or four conductive wires provided for heating and one or two additional conductive wires provided for transferring sensor signals. In other embodiments the conduit may comprise one, two, three or four conductive wires provided for heating and one or two of the same conductive wires are provided for heating and for transferring sensor signals.

Depending on the desired application the one or more electrically conductive wires may be substantially embedded in the enclosing wall or may be substantially exposed to the flow passageway. If more than one electrically conductive wire is provided, one or more wires may be embedded in the enclosing wall while one or more wires may be substantially exposed to the flow passageway. In other embodiments all wires may be embedded in the enclosing wall or all wires may be substantially exposed to the flow passageway.

In embodiments, a conduit is provided wherein the at least one electrically conductive wire comprises an insulating layer and is substantially exposed to the flow passage of said conduit, preferably more than 50% of the surface of the conductive wire is exposed to the flow passage of the conduit, preferably more than 75%, more than 85%, more than 95%, more than 99%. In embodiments, the one or more electrically conductive wires substantially exposed to the flow passageway may also be lying substantially freely within the passageway. This may have the advantage that the wire lies at low points of the flow passageway, where moisture would collect.

In embodiments, a conduit is provided wherein at least one electrically conductive wire is substantially enclosed by the enclosing wall, preferably more than 50% of the surface of the electrically conductive wire is enclosed by the enclosing wall, preferably more than 75%, more than 85%, more than 95%, more than 99%. In embodiments the wire is embedded in the enclosing wall.

In embodiments, as explained above, the conduit comprises a first helically wrapped web. The at least one electrically conductive wire may be substantially enclosed by the first web, preferably more than 50% of the surface of the electrically conductive wire is enclosed by the first web, preferably more than 75%, more than 85%, more than 95%, more than 99%. In embodiments the wire is embedded in the web.

In embodiments at least one of the electrically conductive wires is substantially enclosed by the helical rib, preferably more than 50% of the surface of the electrically conductive wire is enclosed by the helical rib, preferably more than 75%, more than 85%, more than 95%, more than 99%. In embodiments the wire is embedded in the helical rib.

FIGS. 6A, 6B and 6C each show a cross-sectional view of a part of the enclosing wall in axial direction of the conduit in accordance with the invention and demonstrate a non-limiting number of possible arrangements for the one or more electrically conductive wires 10. The type of weld at the interface between the adjacent windings of the web forming the helical rib 7 is not depicted and may be any type discussed before. The electrically conductive wire 10 may comprise an insulating layer and a hydrophilic layer, in accordance with some embodiments of the invention. As shown in FIG. 6A, the one or more electrically conductive wire 10 may be comprised in the helical rib 7 which is bonded to the first helical web 4. As shown in FIG. 6B, the one or more electrically conductive wire 10 may be comprised in the first helical web 4, which is bonded to the helical rib 7. As will be clear to the person skilled in the art, the relative sizes of the electrical wire and the web have been exaggerated for demonstrative purposes. As described earlier, the electrical wire may be completely embedded in the helical web. As shown in FIG. 6C, two or more electrical wires may be provided, one or more embedded in the helical rib and one or more embedded in the web.

In highly preferred embodiments, a conduit as shown in FIG. 6A is provided wherein the one or more electrically conductive wire 10 is comprised in a helical rib 7 which is bonded to a first helical web 4, and wherein the helical rib 7 is of the type shown in FIG. 5B wherein the adjacent turns of the web are separated by a space 29, and the rib comprises a first inner polymer material 8, embedded in a second outer polymer material 9 different from said first inner polymer material, wherein the one or more electrically conductive wire 10 is located in the first inner polymer material 8.

Figure 7:
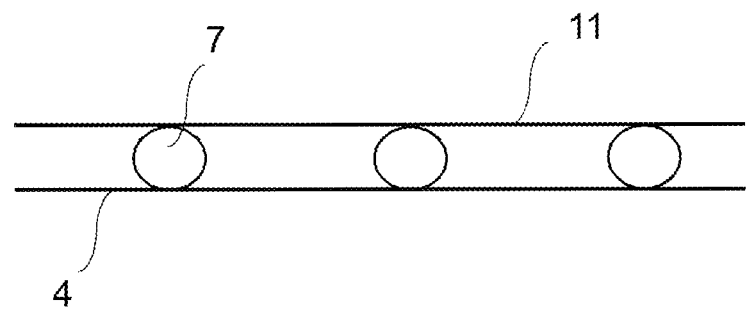
FIG. 7 shows a second helical web 11 which is heat-bonded to a rib 7 opposite to a first web 4.
Figure 8:
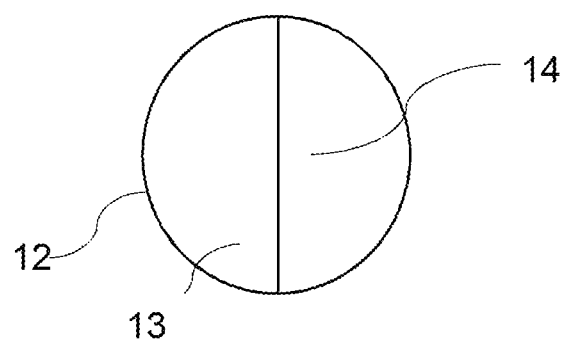
FIGS. 8A and 8B show partitioned conduits in accordance with the invention.
Figure 8:
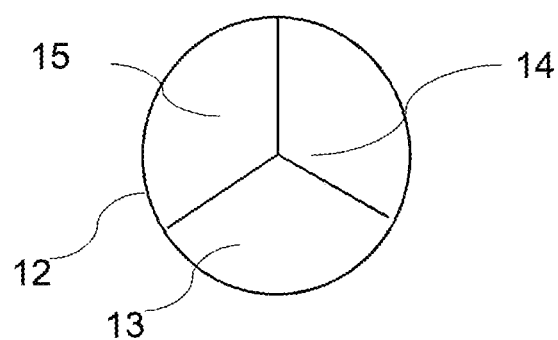

As shown in FIG. 7, for insulation purposes, it may be desirable to include a second helical web 11 which may be heat-bonded to the rib 7 opposite to the first web 4.

In embodiments where the conduit comprises a helically wound profile, the enclosing wall may be characterized by a pitch of 4-10 mm, such as 5-7 mm. The pitch may be constant or may vary in the longitudinal direction of the conduit, which may be desirable to confer variations in flexibility, mechanical properties or conductive wire density (e.g. for heating purposes)—along the length of the conduit.

In embodiments, a conduit is provided wherein the enclosing wall comprises two or more helical ribs, preferably 2, 3 or 4 helical ribs, preferably 2 or 3 helical ribs, preferably 2 helical ribs. The two or more ribs may be separately extruded. The two or more ribs may be characterized by a different pitch, said pitch may be constant or varying in the longitudinal direction of the conduit. The two or more ribs may be different in composition, for example they may each comprise different polymer materials.

In embodiments a conduit is provided wherein the enclosing wall comprises two or more helical ribs and wherein at least one helical rib comprises one or more electrically conductive wires provided for heating, transferring sensor signals or a combination thereof.

In embodiments a conduit is provided wherein the enclosing wall comprises two or more helical ribs, wherein at least one helical rib comprises an electrically conductive wires provided for heating, transferring sensor signals or a combination thereof and wherein at least one helical rib does not comprise an electrically conductive wire.

In embodiments, a conduit as described herein is provided wherein the enclosing wall is characterized by a web thickness of more than 0.03 mm, preferably more than 0.04 mm, more than 0.05 mm, more than 0.06 mm. In embodiments, a conduit as described herein is provided wherein the enclosing wall is characterized by a web thickness of less than 0.5 mm, preferably less than 0.2 mm, less than 0.1 mm.

In embodiments there is provided a conduit for a breathing circuit comprising an inlet, an outlet, and an enclosing wall defining a flow passage between said inlet and said outlet, wherein the enclosing wall is permeable to water vapor and one or more of $O_2$ and $CO_2$, wherein the axial tensile strength of said enclosing wall is greater than 40N preferably greater than 50N, greater than 65N, greater than 80N, greater than 95N or greater than 110N and wherein the enclosing wall is characterized by a web thickness of more than 0.03 mm, preferably more than 0.04 mm, more than 0.05 mm, more than 0.06 mm.

In highly preferred embodiments, there is provided a conduit for a breathing circuit comprising an inlet, an outlet, and an enclosing wall defining a flow passage between said inlet and said outlet, wherein
  the axial tensile strength of said enclosing wall is greater than 40N preferably greater than 50N, greater than 65N, greater than 80N, greater than 95N or greater than 110N
and wherein the enclosing wall is characterized by
  a water vapor transmission rate of at least 0.01 g/(cm$^2$*day), preferably at least 0.05 g/(cm$^2$*day), or at least 0.1 g/(cm$^2$*day), which may be tested in accordance with the WVTR test procedure;
  a $CO_2$ transmission rate of more than 1 cm$^3$/(m$^2$*day*bar), preferably more than 10 cm$^3$/(m$^2$*day*bar), more than 100 cm$^3$/(m$^2$*day*bar), more than 300 cm$^3$/(m$^2$*day*bar) or more than 370 cm$^3$/(m$^2$*day*bar) which may be tested in accordance with the $CO_2$ test procedure; and
  a web thickness of more than 0.03 mm, preferably more than 0.04 mm, more than 0.05 mm, more than 0.06 mm.

In highly preferred embodiments, there is provided a conduit for a breathing circuit comprising an inlet, an outlet, and an enclosing wall defining a flow passage between said inlet and said outlet, wherein
  the axial tensile strength of said enclosing wall is greater than 40N preferably greater than 50N, greater than 65N, greater than 80N, greater than 95N or greater than 110N
and wherein the enclosing wall is characterized by
  a water vapor transmission rate of at least 0.01 g/(cm$^2$*day), preferably at least 0.05 g/(cm$^2$*day), or at least 0.1 g/(cm$^2$*day), which may be tested in accordance with the WVTR test procedure;
  a $CO_2$ transmission rate of more than 1 cm$^3$/(m$^2$*day*bar), preferably more than 10 cm$^3$/(m$^2$*day*bar), more than 100 cm$^3$/(m$^2$*day*bar), more than 300 cm$^3$/(m$^2$*day*bar) or more than 370 cm$^3$/(m$^2$*day*bar) which may be tested in accordance with the $CO_2$ test procedure;
  a $CO_2$ transmission rate of less than 100000 cm$^3$/(m$^2$*day*bar), preferably less than 10000 cm$^3$/(m$^2$*day*bar), less than 1000 cm$^3$/(m$^2$*day*bar), less than 500 cm$^3$/(m$^2$*day*bar) or less than 420 cm$^3$/(m$^2$*day*bar) which may be tested in accordance with the $CO_2$ test procedure; and
  a web thickness of more than 0.03 mm, preferably more than 0.04 mm, more than 0.05 mm, more than 0.06 mm.

In highly preferred embodiments, there is provided a conduit for a breathing circuit comprising an inlet, an outlet, and an enclosing wall defining a flow passage between said inlet and said outlet, wherein
  the axial tensile strength of said enclosing wall is greater than 40N preferably greater than 50N, greater than 65N, greater than 80N, greater than 95N or greater than 110N
and wherein the enclosing wall is characterized by
  a water vapor transmission rate of at least 0.01 g/(cm$^2$*day), preferably at least 0.05 g/(cm$^2$*day), or at least 0.1 g/(cm$^2$*day), which may be tested in accordance with the WVTR test procedure;

a $CO_2$ transmission rate more than 1 $cm^3/(m^2*day*bar)$, preferably more than 10 $cm^3/(m^2*day*bar)$, more than 100 $cm^3/(m^2*day*bar)$, more than 300 $cm^3/(m^2*day*bar)$ or more than 370 $cm^3/(m^2*day*bar)$ which may be tested in accordance with the $CO_2$ test procedure;

an $O_2$ transmission rate of more than 0.1 $cm^3/(m^2*day*bar)$, preferably more than 1 $cm^3/(m^2*day*bar)$, more than 10 $cm^3/(m^2*day*bar)$ or more than 20 $cm^3/(m^2*day*bar)$ which may be tested in accordance with the $O_2$ test procedure; and a web thickness of more than 0.03 mm, preferably more than 0.04 mm, more than 0.05 mm, more than 0.06 mm.

In embodiments, the conduit of the invention is provided as a partitioned conduit, thereby defining two or more flow passages within one conduit. This is shown schematically in FIGS. 8A and 8B. FIG. 8A shows a conduit in accordance with the invention 12 partitioned into a first flow passage 13 and a second flow passage 14. FIG. 8B shows a conduit in accordance with the invention 12 partitioned into a first flow passage 13, a second flow passage 14 and a third flow passage 15. In embodiments, a conduit of the invention is provided as a partitioned conduit consisting of two, three or four flow passages, preferably two or three flow passages, preferably two flow passages.

The conduit of the present invention is advantageously incorporated in a limb for a breathing circuit. Many variations of limbs for breathing circuits are known to the person skilled in the art. A selection of embodiments are explained below but should not be construed as limiting.

Figure 9:
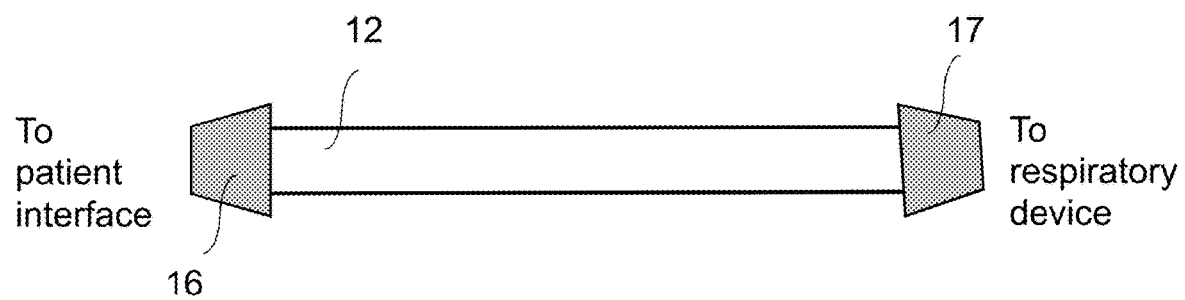
FIG. 9 shows a limb for a breathing circuit comprising at least one conduit 12 according to the invention, a first connector 16 mounted at the first end of the at least one conduit and a second connector 17 mounted at the second end of the at least one conduit.
Figure 10:
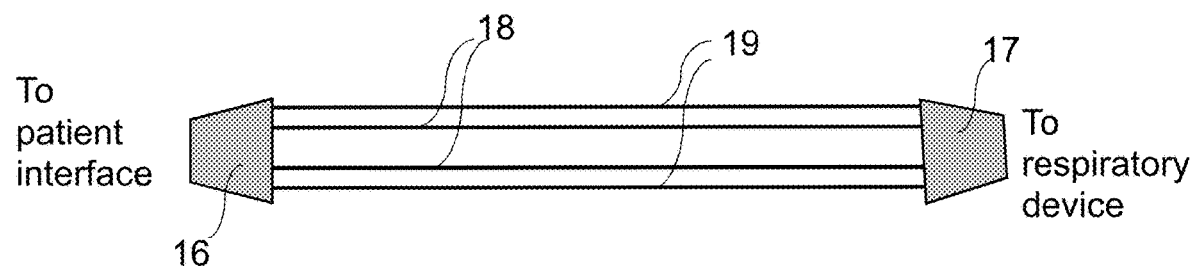
FIGS. 10A, 10B, 10C and 10D show longitudinal and transversal cross sections of a limb which is a coaxial limb comprising an inner conduit 18 and an outer conduit 19 in a coaxial arrangement, defining an inner flow passage 20 within the inner conduit and an outer flow passage 21 between the inner and the outer conduit wherein the inner and/or outer conduit is a conduit according to the invention.
Figure 10:
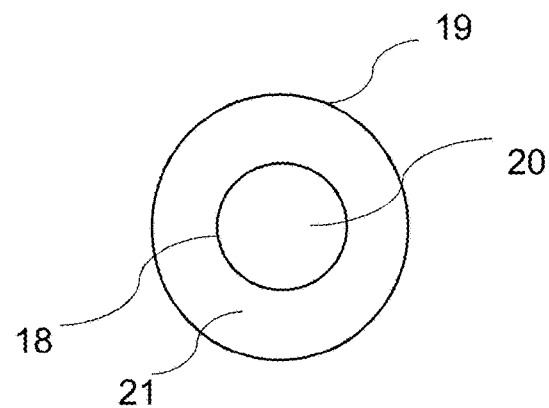
Figure 10:
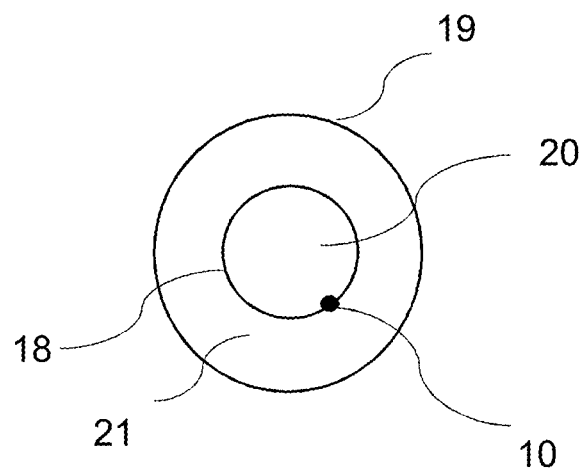
Figure 10:
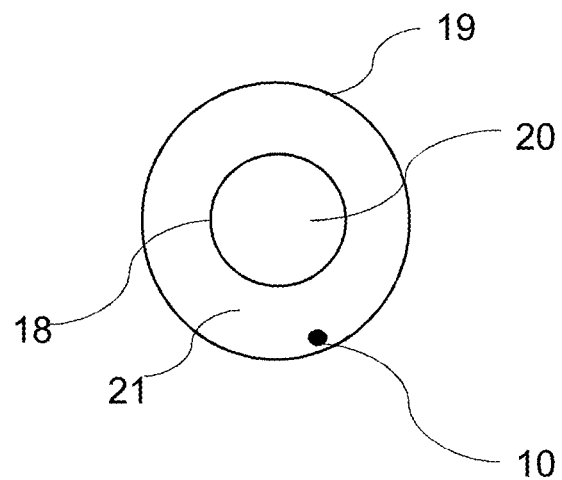
Figure 11:
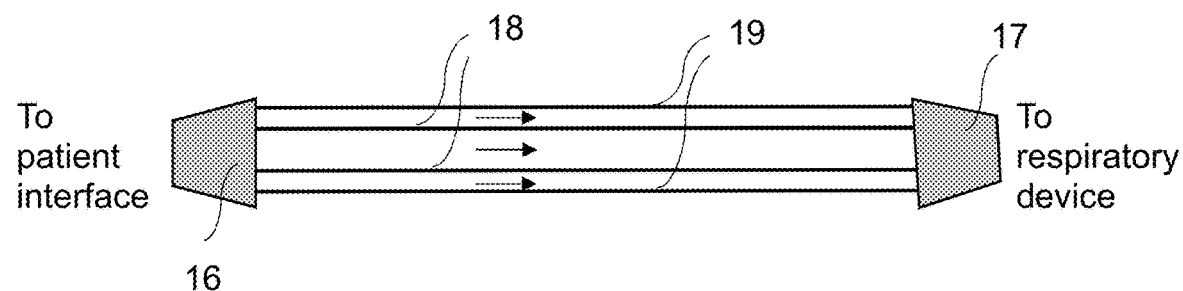
FIGS. 11A, 11B and 11C show longitudinal cross sections of coaxial limbs provided for different directions of gas flow.
Figure 11:
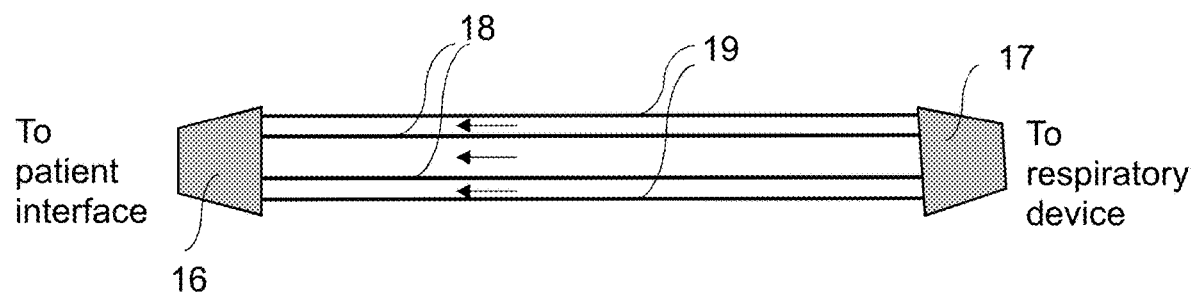
Figure 11:
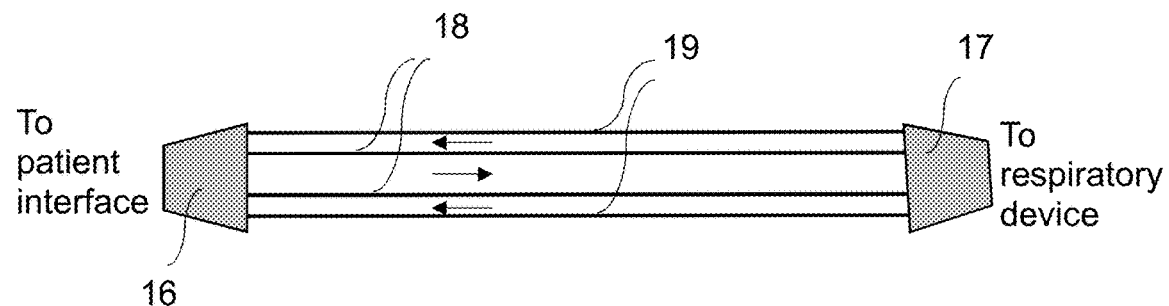

As shown in FIG. 9 there is thus provided a limb for a breathing circuit comprising at least one conduit 12 according to the invention, a first connector 16 mounted at the first end of the at least one conduit and a second connector 17 mounted at the second end of the at least one conduit, wherein the first connector is provided for connecting to a first device of the breathing circuit, for example a patient interface and the second connector is provided for connecting to a second device of the breathing circuit, for example a humidifier, a ventilator or other device. In embodiments, the connectors may be of the same or different types such as male and/or female fittings. In embodiments the connectors may be designed in such a way as to allow swivel connections. The first and second connector may be of the same or different sizes. In embodiments, the first and/or second connector is a cuff. The first and/or second connector or cuff may be manufactured using a number of different techniques, including overmoulding, intrusion moulding, assembly and/or injection moulding. The first and/or second connector or cuff may comprise different materials, for example the bore of the cuff can be made from a harder material allowing easier connection to associated equipment while the outer overmould can be made from a soft touch material to enable easier handling by the patient. The first and/or second connector or cuff may also comprise a securing system to prevent the connector or cuff from accidentally disengaging from the conduit. The first and/or second connector or cuff may comprise means for connecting to one or more electrically conductive wires which may be comprised in the conduit. These and other variations of the first and/or second connector or cuff are known to the person skilled in the art and do not require further explanation.

In embodiments the limb is an inspiratory limb. In embodiments the limb is an expiratory limb. In embodiments the same limb functions as inspiratory and expiratory limb.

In embodiments the limb may further comprise additional reinforcing measures to improve the mechanical strength of the tube. In embodiments such reinforcing measures may include the use of longitudinal reinforcements, such as a reinforcing member lying freely within the conduit and/or a plurality of longitudinal threads.

The first and/or second connector may also act as a through conduit where additional respiratory conduits can be attached to.

In embodiments, as shown in FIGS. 10A (longitudinal cross-section) and 10B (transversal cross-section) a limb as described herein before is provided which is a coaxial limb comprising an inner conduit 18 and an outer conduit 19 in a coaxial arrangement, defining an inner flow passage 20 within the inner conduit and an outer flow passage 21 between the inner and the outer conduit wherein the inner and/or outer conduit is a conduit according to the invention. In embodiments the inner conduit 18 is a conduit according to the invention, i.e. a conduit of high mechanical strength comprising a moisture permeable enclosing wall as described herein earlier. The inner and/or outer conduit may comprise one or more electrically conductive wires provided for heating and/or transferring sensor signals as described herein before. The one or more electrically conductive wires may be comprised in the inner conduit, in the outer conduit, or in both conduits. The term comprised in the inner/outer conduit should be taken to mean at least all embodiments described earlier, such as in the enclosing wall of the conduit, exposed to the flow passage of the conduit etc.

In an embodiment, as shown in FIG. 10C, there is provided a coaxial limb comprising at least one electrically conductive wire 10 provided for heating, transferring sensor signals or a combination thereof, which is substantially embedded in the enclosing wall of the inner conduit J3, preferably more than 50% of the surface of the conductive wire is embedded in the enclosing wall of the inner conduit, preferably more than 75%, more than 85%, more than 95%, more than 99%. In embodiments, the wire is enclosed in the web part of the inner conduit. In embodiments the wire is enclosed in the rib part of the inner conduit. In embodiments two or more electrically conductive wires are provided, one enclosed in the web part of the inner conduit and one enclosed in the rib part of the inner conduit. In an embodiment, as shown in FIG. 10D, there is provided a coaxial limb as described above comprising at least one electrically conductive wire 10 provided for heating, transferring sensor signals or a combination thereof, which is substantially exposed to the outer flow passage, preferably more than 50% of the surface of the conductive wire is exposed to the outer flow passage, preferably more than 75%, more than 85%, more than 95%, more than 99%.

The coaxial limb may be provided in a number of different flow passage configurations for different purposes, depending for example on the connector. In embodiments there is provided a coaxial limb wherein both the inner and outer flow passages form an expiratory flow path, as shown in FIG. 11A wherein the arrow indicates the direction of gas flow. In embodiments there is provided a coaxial limb wherein both the inner and outer flow passages form an inspiratory flow path as shown in FIG. 11B. In embodiments there is provided a coaxial limb wherein the inner flow passage forms an expiratory flow path and the outer flow passage forms an inspiratory flow path as shown in FIG. 11C.

Alternatively, a coaxially insulated limb may be provided comprising an inner conduit in accordance with the invention and an insulating outer layer in a coaxial arrangement wherein the insulating outer layer comprises an enclosing wall characterized by a water vapor transmission rate which is the same or higher than that of the enclosing wall of the inner conduit.

Figure 12:
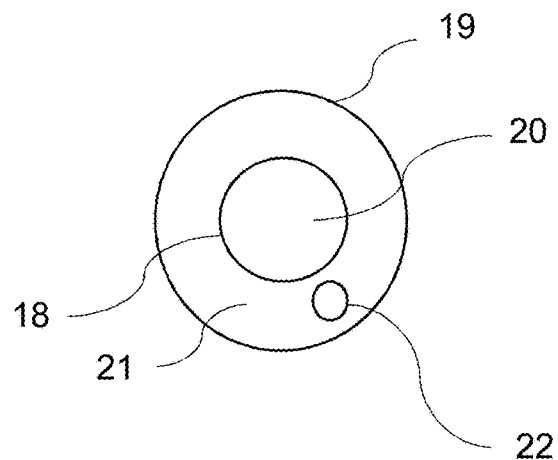
FIG. 12 shows a transversal cross-section of a coaxial limb comprising a third conduit 22 located within the outer flow passage 21 defined by the space between the inner conduit 18 and an outer conduit 19.

As shown in FIG. 12, in embodiments there is provided a coaxial limb as described earlier comprising a third conduit 22 located within the outer flow passage 21 defined by the space between the inner conduit 18 and an outer conduit 19, wherein the inner and/or outer conduit is a conduit according to the invention. The third conduit 22 may be useful for e.g. supplying additional oxygen to a patient or as a pressure sensing line.

Figure 13:
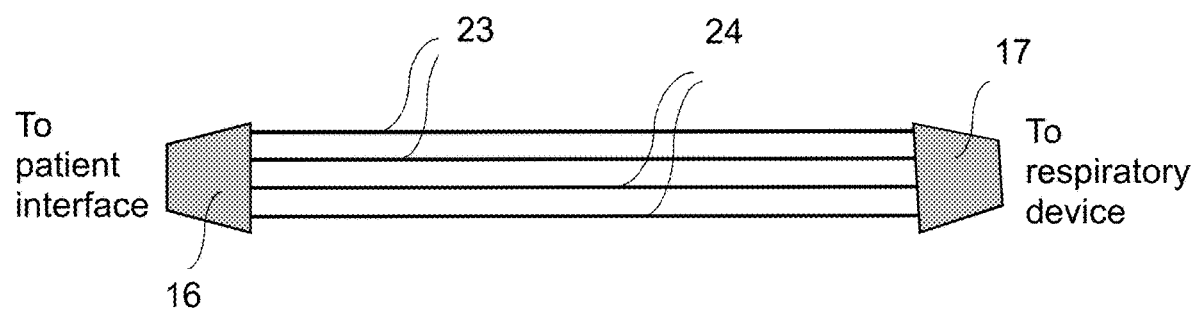
FIG. 13 shows a longitudinal cross section of a parallel limb comprising a first conduit 23 and a second conduit 24 in a parallel arrangement wherein the first connector is connected to both the first and the second conduit.
Figure 14:
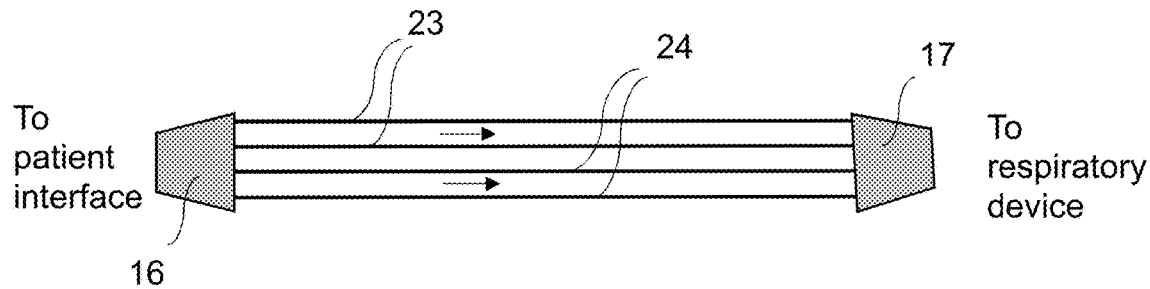
FIGS. 14A, 14B and 14C show longitudinal cross sections of parallel limbs provided for different directions of gas flow.
Figure 14:
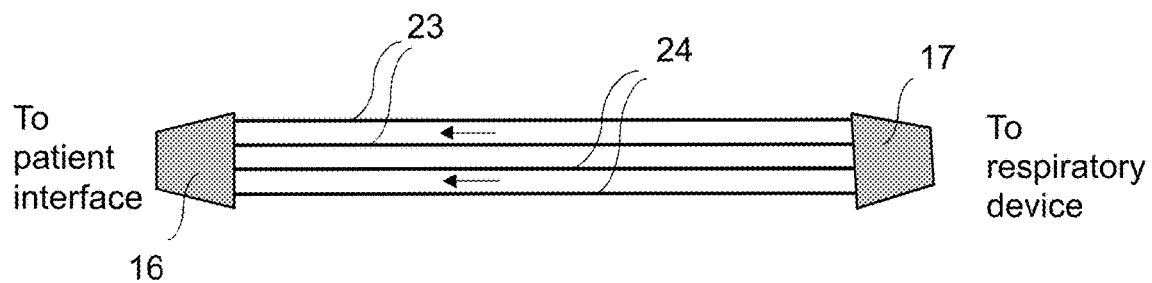
Figure 14:
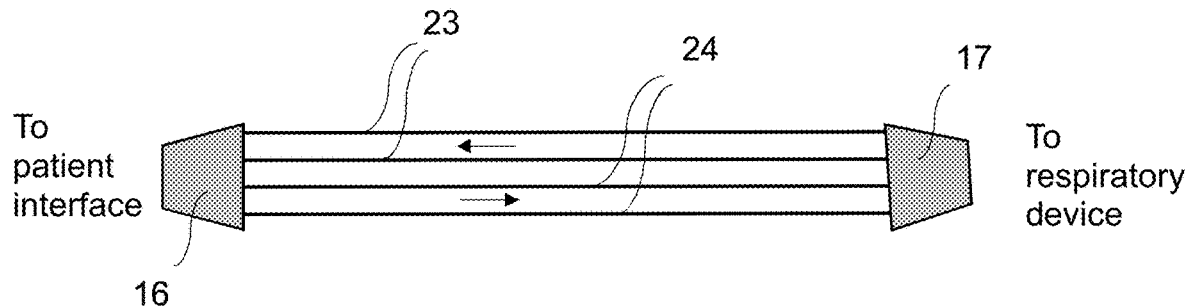
Figure 15:
FIGS. 15A, 15B, 15C and 15D illustrate how a profile comprising adjacent windings of a first web 4 attached to a first rib part 25 which has at least one valley shaped area 26, at least one electrically conductive wire 10 and a second rib part 27 may be formed.
Figure 15:
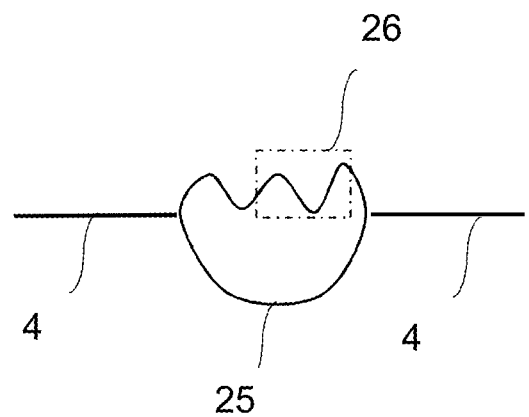
Figure 15:
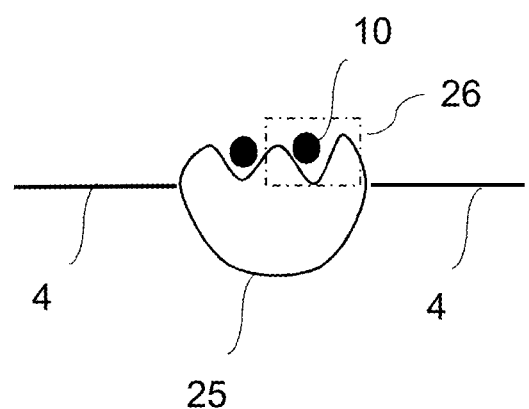
Figure 15:
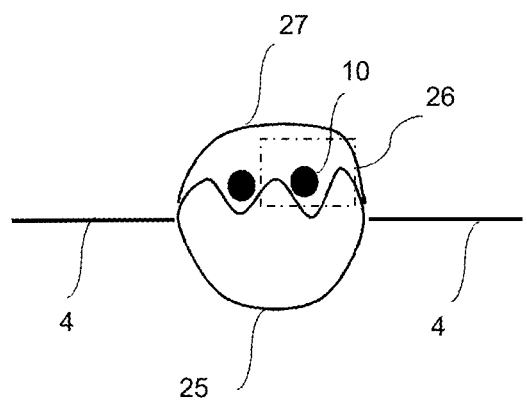

As shown in FIG. 13, in embodiments there is provided a limb as described earlier which is a parallel limb comprising a first conduit 23 and a second conduit 24 in a parallel arrangement wherein the first connector is connected to both the first and the second conduit. As used herein, the term parallel merely indicates that the first and second conduits are not coaxially arranged and should not be interpreted to limit the parallel limb in any other way. The parallel limb may comprise three, four or more conduits. At least one, preferably all conduits are conduits according to the invention. The first and/or second conduit may comprise one or more electrically conductive wires provided for heating and/or transferring sensor signals as described herein before. The one or more electrically conductive wires may be comprised in the first conduit, in the second conduit, or in both conduits. The term comprised in the first/second conduit should be taken to mean at least all embodiments described earlier, such as in the enclosing wall of the conduit, exposed to the flow passage of the conduit etc. As shown in FIG. 14A, in embodiments there is provided a parallel limb wherein the first and second conduits form an expiratory flow path. As shown in FIG. 14B, in embodiments there is provided a parallel limb wherein the first and second conduits form an inspiratory flow path. As shown in FIG. 14C, in embodiments there is provided a parallel limb wherein the first conduit forms an inspiratory flow path and the second conduits form an expiratory flow path. It has also be found that, in order to provide an unobstructed breathing experience, it is preferred that the combined inner diameter of the first and second conduits is larger than or equal to the inner diameter of the first connector.

In another aspect of the invention there is provided a breathing circuit comprising at least one limb in accordance with the invention, a first device of the breathing circuit, for example a patient interface and a second device of the breathing circuit, for example a humidifier, a ventilator or other device. The breathing circuit may be an open or closed breathing circuit. In embodiments the breathing circuit is a closed breathing circuit such as an anesthesia breathing circuit. In embodiments the breathing circuit is an open breathing circuit such as a continuous positive airway pressure (CPAP) breathing circuit. As used herein, the term "closed breathing circuit" also comprises partial rebreathing circuits, also known as semi-closed circuits.

The conduits in accordance with the invention may be prepared using a process comprising common polymer processing techniques known to the skilled person such as extrusion, spiral winding, blow-moulding, etc.

In embodiments according to the invention there is provided a method of producing a flexible conduit, comprising:
  a) providing at least a first polymer material or blend,
  b) optionally providing a second polymer material or blend
  c) extruding at least one rib,
  d) extruding at least one web, and
  e) forming said conduit by helically winding said at least one web and joining adjacent windings of said at least one web by means of said at least one rib,
  wherein said first polymer material or blend is used for at least a first web among said at least one web and is a predetermined material or blend, selected for making said first web permeable to water vapor and one or more breathing gases as described herein before.

In embodiments the method provided herein comprises extruding the at least one rib onto the at least one web while the at least one web is being displaced axially wherein the at least one rib is heat bonded to the at least one web. The method provided herein may comprise the use of a co-extrusion die, or separate dies to create the at least one rib and at least one web separately, whereafter they are bonded. Preferably two separate dies are used.

In embodiments there is thus provided the method described earlier wherein at least two extruders are employed, one being utilized to continuously form at least one web which is displaced axially as it is formed, and the other extruder being utilized to deposit at least one rib on the at least one web while it is being displaced axially, wherein the at least one rib is heat bonded to the at least one web.

In embodiments, the extruder provided for continuously forming at least one rib, is placed substantially above the at least one web which is being axially displaced.

A preferred embodiment of the method of producing a flexible conduit described above is provided, comprising:
  a) providing a first polymer material or blend,
  b) providing a second polymer material or blend different from the first polymer material or blend,
  c) extruding the first polymer material or blend into a first rib,
  d) extruding the second polymer material or blend into a first web, and
  e) forming said conduit by helically winding said first web and joining adjacent windings of said first web by means of said first rib,
  wherein said first polymer material or blend is used for at least a first web among said at least one web and is a predetermined material or blend, selected for making said first web permeable to water vapor and one or more further breathing gases as described herein before.

In embodiments the methods above are provided wherein the conduit is a conduit in accordance with the invention as described herein before.

In embodiments, the methods above are provided wherein step c) comprises extruding the rib at a temperature within the range of 190-280° C., preferably 210-270° C., preferably 220-260° C., preferably 230-250° C., preferably 235-245° C.

In embodiments, the methods above are provided wherein step d) comprises extruding the web at a temperature within the range of 170-260° C., preferably 180-250° C., preferably 190-240° C., preferably 200-230° C., preferably 210-220° C.

Without wishing to be bound by any theory, the present inventors have surprisingly found that the improved tensile strength observed with the conduits of the present invention may be related to a cooling step applied to the web before or during winding.

Thus, in embodiments step e) of the methods described above further comprises cooling one of the at least one webs and/or cooling one of the at least one ribs before or during winding. This may be achieved by any cooling means such as cold air, running the extruded web through a water bath, employing an internally or externally cooled mandrel, employing an internally or externally cooled roller, and any combination thereof.

In preferred embodiments the at least one web is cooled to a temperature within the range of 120-210° C., preferably 130-190° C., preferably 140-185° C., preferably 150-180° C., preferably 160-170° C. before or during winding.

In preferred embodiments the at least one rib has a temperature within the range of 150-240° C., preferably 160-230° C., preferably 170-210° C., preferably 175-200° C., preferably 185-195° C. before or during winding.

In embodiments, the method as described above is provided wherein the second polymer material provided in step b) is characterized by at least one of the following:

a water vapor transmission rate at 23° C. and 85% relative humidity of 30-3000 g/(m$^2$*day), preferably 60-1500 g/(m$^2$*day), preferably 120-750 g/(m$^2$*day), preferably 240-375 g/(m$^2$*day), preferably 280-320 g/(m$^2$*day), tested in accordance with DIS 15106-1/2 on a 0.025 mm thick film;

an oxygen transmission rate at 23° C. and 85% relative humidity of 200-60000 cm$^3$/(m$^2$*day*bar), preferably 500-30000 cm$^3$/(m$^2$*day*bar), preferably 1000-15000 cm$^3$/(m$^2$*day*bar), preferably 2500-10000 cm$^3$/(m$^2$*day*bar), preferably 5000-7000 cm$^3$/(m$^2$*day*bar), preferably 5800-6200 cm$^3$/(m$^2$*day*bar), tested in accordance with DIS 15105-1/2 on a 0.025 mm thick film; and/or a $CO_2$ transmission rate at 25° C. and 85% relative humidity of 10000-200000 cm$^3$/(m$^2$*day*bar), preferably 20000-150000 cm$^3$/(m$^2$*day*bar), preferably 50000-100000 cm$^3$/(m$^2$*day*bar), tested in accordance with DIS 15105-1/2 on a 0.025 mm thick film.

In embodiments the second polymer material is selected from the group consisting of polyethyleneterephtalate esters (PET), polybutyleneterephtalate esters (PBT), polyvinylidene fluorides (PVDF), ethylene acrylic acid copolymers (EAA), polypropylenes (PP), fluorinated ethylene propylene copolymers (FEP), liquid crystal polymers (LCP), polytetrafluoroethylenes (PTFE), TPU (e.g. polyether TPU) and polybutyleneterephtalate block copolyesters, preferably polybutyleneterephtalate block copolyesters.

In embodiments, the second polymer material is selected from one or more of the following: Kraton D2104, Kraton D1101, Kraton G1652, Kraton G2705, Estane 58245, Estane MVT (such as MVT 90 NT1, MVT 80 NT1 or MVT 75AT3), Pebax MV 3000 SP 01, Arnitel VT (such as VT3108, VT3118 or VT 7812), Pebax MV6100, Nylon 66, Cyclolac 1033 and Hytrel 5556, preferably Arnitel VT3108, Arnitel VT3118, Arnitel VT7812 and Arnitel VT3104, preferably Arnitel VT3108 and Arnitel VT3104, most preferably Arnitel VT3108. In preferred embodiments, the second polymer material is selected from one or more of the following commercially available material brands: Hytrel, Arnitel. In more preferred embodiments the second polymer material is one or more of the following commercially available materials: Arnitel VT3108, Arnitel VT3118, Arnitel VT7812 or Arnitel VT3104, preferably Arnitel VT3108 or Arnitel VT3104, most preferably Arnitel VT3108.

In embodiments the methods provided herein comprise forming a helically wound profile as shown in FIG. 15D. FIGS. 15A, 15B, 15C and 15D illustrate how such a profile may be formed by providing two non-overlapping adjacent windings of the first web 4, extruding a first rib part 25 which has at least one valley shaped area 26, for example 2 valley shaped areas 26 and binding the first rib part 25 to the two non-overlapping adjacent windings of the first web 4. At least one electrically conductive wire 10 is placed in the at least one valley shaped area 26 and covered with a second extruded rib part 27.

This method of manufacturing has several advantages, such as increased manufacturing efficiency due to easy and reproducible wire placement and easier automatisation of subsequent manufacturing steps since the transition or 'seam' between the first rib part 25 and the second rib part 27 allows easy access to the at least one electrically conductive wire 10, for example to attach an interface.

A preferred embodiment of the method of producing a flexible conduit described herein earlier is provided, comprising:
a) providing a first polymer material or blend,
b) providing a second polymer material or blend different from the first polymer material or blend,
c) extruding the first polymer material or blend into a first rib part 25 which has at least one valley shaped area 26,
d) extruding the second polymer material or blend into a first web 4,
e) forming said conduit by helically winding said first web and joining adjacent windings of said first web by means of said first rib part 25,
f) placing at least one electrically conductive wire 10 in the at least one valley shaped area 26, and
g) covering said electrically conductive wire 10 with a second extruded rib part 27, wherein said first polymer material or blend is used for at least a first web among said at least one web and is a predetermined material or blend, selected for making said first web permeable to water vapor and one or more further breathing gases as described herein before.

In a further aspect of the invention, the use of the limb in accordance with the invention to remove water vapor from a gas stream, preferably a patient gas stream is provided. In embodiments the limb is used to remove water vapor and $CO_2$ from a gas stream, preferably a patient gas stream. In embodiments said gas stream is an expiratory gas stream. In embodiments said gas stream is an inspiratory gas stream.

In embodiments the uses provided herein comprise a reduction of the relative humidity of the gas stream, determined at the inlet and the outlet of the conduit, by more than 5%, preferably by more than 10%, preferably by more than 20%. In embodiments the uses provided herein comprise the removal of more than 1 g, preferably more than 10 g, preferably more than 50 g of water from the gas stream, determined over 24 hours, for example when the gas stream is a patient expiratory gas stream.

In embodiments the uses provided herein comprise a reduction of the $CO_2$ content of the gas stream, determined at the inlet and the outlet of the conduit. In embodiments said reduction is more than 0.1%, such as more than 1%, more than 5% or more than 10%. In embodiments said reduction is less than 80%, such as less than 50%, less than 40% or less than 20%.

It is understood that the present disclosures of the different embodiments of the invention have been made only by way of example, and that numerous changes in the details of construction and the method of production may be resorted to without departing from the spirit and scope of the invention.

Example 1

Two conduits in accordance with the invention were prepared by extruding Arnitel VT3108 into a web at 215° C. and extruding Arnitel EM630 (98% EM630+2% white master batch) into a rib at 240° C. The web was cooled to 165° C. and the rib was cooled to 190° C.; subsequently the web was wound and adjacent windings of the web were joined to the rib in a manner such that adjacent windings of the web were not overlapping. The conduits were of the type as shown in FIG. 4B with two copper heating wires embedded in the helical rib.

The resulting conduit has an inner diameter of 18.3 mm, a web thickness of 0.07 mm, a pitch of 5.8 mm and was cut to a first piece of a length of 1562 mm (in between cuffs) and a second piece of a length of 1705 mm (in between cuffs).

Figure 16:
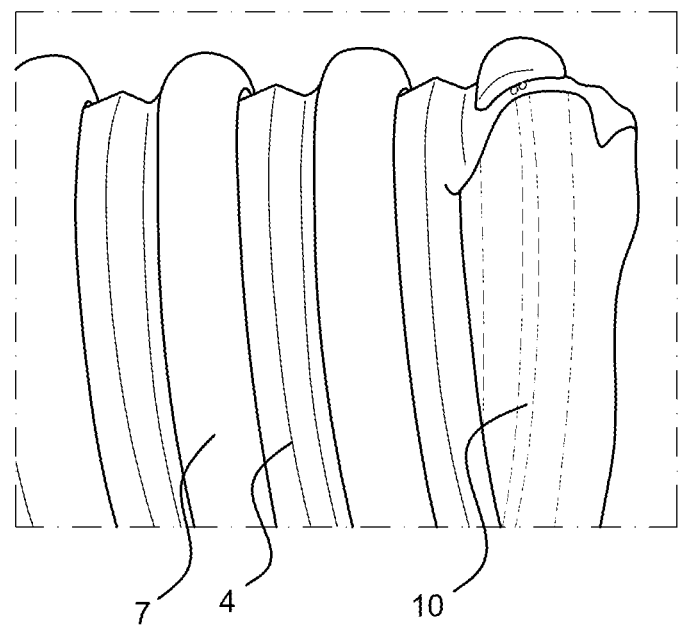
FIG. 16 shows part of the conduit of example 1 comprising a transparent first web 4, a rib 7 and electrically conductive wires 10, in particular heating wires, embedded in the rib.

FIG. 16 shows part of a conduit of example 1, comprising a transparent first web 4, a rib 7 and electrically conductive wires 10, in particular heating wires, embedded in the rib.

Example 2

The water vapor transmission rate of the 1705 mm conduit prepared in example 1 was tested at an ambient temperature of 23° C. and an ambient humidity of 35% RH.

Compressed air of <5% RH was humidified by a humidifier mounted before the conduit to approximately 100% RH and fed via a splitter to the conduit of example 1 and a 'non-breathable' control conduit (metallocene PE) at a rate of 7.5 liter per minute (for each conduit) for 24 hours. The conduit of example 1 was heated at 18 Watt. After passing through the conduits, the air from each conduit was led to a water trap and the the amount of water collected in the trap over 24 hours determined based on the weight of the trap before the experiment and after 24 hours.

For comparative purposes, the water vapor transmission rate of a commercially available 'breathable' conduit (evaqua 2) was tested using the same procedure but heated at 20 Watt. Evaqua 2 is a non-transparent blow molded hose which is marketed as a 'breathable' limb for a breathing apparatus.

The results are shown in the below table.

| | Mass water in water trap - 24 h (g) | Difference to control (g) | Inner surface area (cm$^2$) | Water Vapor transmission rate (g/(cm$^2$*day)) |
|---|---|---|---|---|
| Example 1 (length 1705 mm; 18 Watt) | 94.9 | 127 | 985 | 0.12 |
| Evaqua 2 (length 1620 mm; inner diameter 18 mm, 20 Watt) | 67.4 | 154.5 | 921 | 0.16 |
| Metallocene PE (control) | 221.9 | — | — | — |

As can be seen from the table, the conduit of example 1 has a high water vapor transmission rate.

Example 3

The $O_2$ transmission rate of a conduit prepared in example 1 was tested at 38° C. using the system MOCON OX-TRAN 2/21 MH by cutting the conduit to a piece of 10 cm length and closing the inlet and the outlet of the resulting 10 cm conduit by gluing each of the inlet and the outlet to a metal plate using epoxy glue. One of the metal plates was mounted with tubing to allow flushing the flow passage of the conduit with carrier gas ($N_2/H_2$). The conduit was placed in a glass chamber which was flushed with 1% Oxygen (in $N_2$) and the Oxygen Transmission Rate from the glass chamber into the conduit was determined using a coloux sensor which analyzes the carrier gas. The relative humidity of the carrier gas was 86%. The gas flow was set low such that the experiment was performed at barometric pressure on both sides of the sample. The results are shown in the below table.

| Sample | Results cm$^3$/(piece*day*bar) |
|---|---|
| Example 1 | 0.133 |

Based on the inner surface area of 63 cm$^2$ the oxygen ($O_2$) transmission rate of the conduit prepared in example 1 is calculated as 0.00211 cm$^3$/(cm$^2$*day*bar) or 21 cm$^3$/(m$^2$*day*bar).

Example 4

The $CO_2$ transmission rate of a conduit prepared in example 1 was tested at 38° C. using the system MOCON PERMATRAN-C 4/41 by cutting the conduit to a piece of 10 cm length and closing the inlet and the outlet of the resulting 10 cm conduit by gluing each of the inlet and the outlet to a metal plate using epoxy glue. One of the metal plates was mounted with tubing to allow flushing the flow passage of the conduit with carrier gas ($N_2/H_2$). The carrier gas was dry (relative humidity approximately 0%). The conduit was placed in a glass chamber which was flushed with 4% carbon dioxide (in $N_2$) and the Carbon Dioxide Transmission Rate from the glass chamber into the conduit was determined using a coloux sensor which analyzes the carrier gas. The gas flow was set low such that the experiment was performed at barometric pressure on both sides of the sample The results are shown in the below table.

| Sample | Results cm$^3$/(piece*day*bar) |
|---|---|
| Example 1 | 2.464 |

Based on the inner surface area of 63 cm$^2$ the carbon dioxide ($CO_2$) transmission rate of the conduit prepared in example 1 is calculated as 0.039 cm$^3$/(cm$^2$*day*bar) or 391 cm$^3$/(m$^2$*day*bar).

Example 5

The liquid water removal rate of the conduits prepared in example 1 was tested in a climate controlled room at 22° C. and 35% RH and the conduit was preconditioned in this room for 12 hours preceding the test. The weight of the conduits was recorded and the conduits were suspended in a "u" shape using clamps such that the inlet and outlet of the conduit were at the same height and facing upwards relative to the floor. Next, the conduits were almost completely filled with water, the inlet and outlet were closed with parafilm (a material with low water permeability) and the liquid water removal rate was monitored by recording the water level relative to the starting level every hour. After eight hours, the test was stopped and the weight of the conduit and of the remaining water was recorded. The test was performed in duplicate.

|  |  | Test 1 weight (gram) | Test 2 weight (gram) |
|---|---|---|---|
| START | Conduit | 120.5 | 120.2 |
|  | H$_2$O in conduit | 400 | 430 |
| END | Conduit | 125.6 | 125.8 |
|  | H$_2$O in conduit | 335.8 | 366.8 |

|  | Water level decrease (cm) | |
|---|---|---|
| Time (hours) | Test 1 | Test 2 |
| 0 | 0 | 0 |
| 1 | 3.5 | 4.7 |
| 2 | 4.7 | 5.7 |
| 3 | 5.7 | 6.7 |
| 4 | 7.1 | 8.1 |
| 5 | 7.7 | 9 |
| 6 | 8.9 | 10.1 |
| 7 | 10.1 | 11.3 |
| 8 | 11.1 | 12 |

The starting level of the water was 18 cm under the inlet/outlet for test 1 and 11 cm under the inlet/outlet for test 2. The exposed inner surface area of the conduit is thus 800 cm$^2$ for test 1 and 922 cm$^2$ for test 2. The liquid water removal rate calculated based on the amount of water removed over 8 hours and the exposed surface area is thus 0.01 g/(cm$^2$*hour) for test 1 and 0.009 g/(cm$^2$*hour) for test 2.

Example 6

The tensile strength of the conduit prepared in example 1 was may be tested by mounting a piece of conduit between two clamps at room temperature, stretching the tube in the axial direction and using a Mecmesin PFI 200 force gauge to determine the amount of force applied when breakage occurs, wherein breakage can be observed visually and/or by a drop in the force measured.

For comparative purposes, the tensile strength of commercially available conduits were tested using the same procedure.

Evaqua 1 is a helically wound conduit which has been marketed as a limb for a breathing apparatus with additional longitudinal reinforcing measures to improve the mechanical strength, including both a reinforcing member lying freely within the conduit and a plurality of longitudinal threads.

Evaqua 2 is a non-transparent blow molded hose which is marketed as a limb for a breathing apparatus.

The results are shown in the below table.

|  | Tensile strenght (N) | Web thickness (mm) |
|---|---|---|
| Conduit from example 1 | 113.2 | 0.07 |
| Evaqua 1 | 195 | 0.027 |
| Evaqua 1 without external reinforcements | 22.2 | 0.027 |
| Evaqua 2 | 192 | 0.6 |

From the above examples, it can be seen that the conduit of the invention shows a surprisingly improved tensile strength (more than 5 times that of evaqua 1, with only approximately double the web thickness) without any need for external reinforcements. Additionally, the water vapor transmission rate is comparable to the water vapor transmission rate of the commercially available conduits, while the web of the conduit in accordance with the invention may advantageously be transparent.

Example 7

Figure 17:
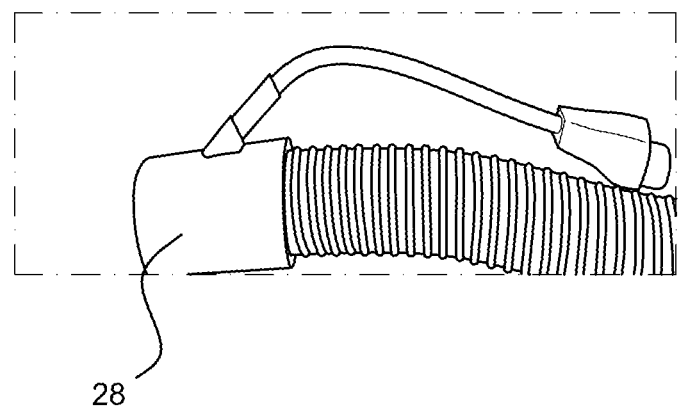
FIG. 17 shows part of the limb of example 7 comprising a cuff 28 which is suitable for connecting to a breathing apparatus and comprises an interface for connecting the embedded heating wires.

The conduit of example 1 was mounted with cuffs to provide a limb for a breathing circuit. FIG. 17 shows the outlet part of the conduit of example 1, mounted with a cuff 28 which is suitable for connecting to a breathing apparatus and comprises an interface for connecting the embedded heating wires.

The invention claimed is:

1. A limb for a breathing circuit comprising:
   at least one flexible, helically wound conduit for a breathing circuit comprising:
     an inlet,
     an outlet, and
     a tubular structure defining a flow passage between said inlet and said outlet,
     wherein said tubular structure consists of a first helical web and a first helically wound rib,
     wherein the first helically wound rib is heat-bonded to adjacent turns of said first helical web,
     wherein said first helical web has a web thickness of less than 0.5 mm, and
     wherein at least a region of said first helical web is made of a predetermined first polymer material or blend, such that the first helical web is permeable to water vapor and one or more of O$_2$ and CO$_2$, and
     wherein the axial tensile strength of the tubular structure by itself is greater than 40N;
   a first connector mounted at the first end of the at least one conduit; and
   a second connector mounted at the second end of the at least one conduit,
   wherein the first connector is provided for connecting to a first device of the breathing circuit and the second connector is provided for connecting to a second device of the breathing circuit.

2. The limb according to claim 1, characterized by a CO$_2$ transmission rate of more than 1 cm$^3$/(m$^2$*day*bar).

3. The limb according to claim 2, characterized by a CO$_2$ transmission rate of less than 100000 cm$^3$/(m$^2$*day*bar).

4. The limb according to claim 3, where the CO$_2$ transmission rate is less than 10000 cm$^3$/(m$^2$*day*bar).

5. The limb according to claim 2, wherein the CO$_2$ transmission rate is more than 10 cm$^3$/(m$^2$*day*bar).

6. The limb according to claim 1, characterized by a water vapor transmission rate of at least 0.01 g/(cm$^2$*day).

7. The limb according to claim 6, wherein the water vapor transmission rate is at least 0.05 g/(cm$^2$*day).

8. The limb according to claim 1, wherein the tubular structure is permeable to liquid water.

9. The limb according to claim 8, wherein the tubular structure is characterized by a liquid water removal rate of more than 0.0001 g/(cm$^2$*hour).

10. The limb according to 9, where the enclosing wall is characterized by a liquid water removal rate of more than 0.0005 g/(cm$^2$*hour).

11. The limb according to claim 1, wherein the first helical web has low haze.

12. The limb according to claim 1, wherein adjacent turns of the web are separated by a space.

13. The limb according to claim 1, wherein the first helically wound rib comprises a first inner polymer material, partially embedded, preferably embedded in a second outer polymer material different from said first inner polymer material.

14. The limb according to claim 1, comprising one or more electrically conductive wires provided for heating, transferring sensor signals or a combination thereof.

15. The limb according to claim 1, which is a coaxial limb comprising an inner conduit and an outer conduit in a coaxial arrangement, defining an inner flow passage within the inner conduit and an outer flow passage between the inner and the outer conduit wherein the inner and/or outer conduit is the at least one conduit.

16. The limb of claim 1, where the axial tensile strength of the enclosing wall is greater than 50N.

17. A method of producing a limb with at least one flexible, helically wound conduit according to claim 1 comprising:
 a) providing a first polymer material or blend,
 b) providing a second polymer material or blend different from the first polymer material or blend,
 c) extruding the first polymer material or blend into a first web with a web thickness of less than 0.5 mm,
 d) extruding the second polymer material or blend into a first rib, and
 e) forming said tubular structure of said conduit by helically winding said first web and joining adjacent windings of said first web by means of said first rib,
 wherein said first polymer material or blend is a predetermined material or blend, selected for making said first web permeable to water vapor and one or more of $O_2$ and $CO_2$ and wherein a cooling step is applied to the first web before it is joined to the first rib.

18. A method of producing a limb with at least one flexible, helically wound conduit according to claim 1, comprising:
 a) providing a first polymer material or blend,
 b) providing a second polymer material or blend different from the first polymer material or blend,
 c) extruding the first polymer material or blend into area first web with a web thickness of less than 0.5 mm,
 d) extruding the second polymer material or blend into a first rib part which has at least one valley shaped area,
 e) forming said tubular structure of said conduit by helically winding said first web and joining adjacent windings of said first web by means of said first rib part,
 f) placing at least one electrically conductive wire in the at least one valley shaped area, and
 g) covering said electrically conductive wire with a second extruded rib part,
 wherein said first polymer material or blend is a predetermined material or blend, selected for making said first web permeable to water vapor and one or more of $O_2$ and $CO_2$ and wherein a cooling step is applied to the first web before it is joined to the first rib part.

19. A method of circulating breathing gases of a patient comprising:
 providing a limb according to claim 1, wherein the first connector is connected to a patient interface and the second connector is connected to a closed-system breathing apparatus comprising a $CO_2$ scrubber;
 circulating breathing gases through the closed-system breathing apparatus; and
 transmitting at least some $CO_2$ from said breathing gases through the enclosing wall of said conduit.

* * * * *